United States Patent
Massimini et al.

(10) Patent No.: US 11,717,139 B2
(45) Date of Patent: Aug. 8, 2023

(54) PLASMA CREATION VIA NONAQUEOUS OPTICAL BREAKDOWN OF LASER PULSE ENERGY FOR BREAKUP OF VASCULAR CALCIUM

(71) Applicants: Boston Scientific Scimed, Inc., Maple Grove, MN (US); Bolt Medical, Inc., Carlsbad, CA (US)

(72) Inventors: Daniel Massimini, Brooklyn Park, MN (US); Roger McGowan, Otsego, MN (US); Haiping Shao, Plymouth, MN (US); Christopher A. Cook, Laguna Niguel, CA (US)

(73) Assignees: Bolt Medical, Inc., Carlsbad, CA (US); Boston Scientific Scimed, Inc., Maple Grove, MN (US)

( * ) Notice: Subject to any disclaimer, the term of this patent is extended or adjusted under 35 U.S.C. 154(b) by 510 days.

(21) Appl. No.: 16/874,065

(22) Filed: May 14, 2020

(65) Prior Publication Data

US 2020/0397230 A1 Dec. 24, 2020

Related U.S. Application Data

(60) Provisional application No. 62/965,069, filed on Jan. 23, 2020, provisional application No. 62/863,506, filed on Jun. 19, 2019.

(51) Int. Cl.
*A61B 18/20* (2006.01)
*A61B 5/1459* (2006.01)
(Continued)

(52) U.S. Cl.
CPC .......... *A61B 1/00082* (2013.01); *A61B 5/027* (2013.01); *A61B 5/1459* (2013.01); *A61B 18/20* (2013.01); *A61B 2017/00057* (2013.01)

(58) Field of Classification Search
CPC ... A61B 1/00082; A61B 5/027; A61B 5/1459; A61B 18/20; A61B 18/26; A61B 2017/00057; A61B 2018/263
See application file for complete search history.

(56) References Cited

U.S. PATENT DOCUMENTS 4,649,924 A 3/1987 Taccardi
4,699,147 A 10/1987 Chilson et al.
(Continued)

FOREIGN PATENT DOCUMENTS

AU 2017205323 1/2022
AU 2019452180 1/2022
(Continued)

OTHER PUBLICATIONS

Provisional International Search Report and Written Opinion dated Feb. 19, 2021 in PCT Application Serial No. PCT/US2020/059960.
(Continued)

*Primary Examiner* — Peter Luong
(74) *Attorney, Agent, or Firm* — Roeder & Broder LLP; James P. Broder

(57) ABSTRACT

A catheter system for treating a treatment site within or adjacent to a blood vessel includes a power source, a light guide and a plasma target. In various embodiments, the light guide receives power from the power source. The light guide has a distal tip, and the light guide emits light energy in a direction away from the distal tip. The plasma target is spaced apart from the distal tip of the light guide by a target gap distance. The plasma target is configured to receive light energy from the light guide so that a plasma bubble is generated at the plasma target. The power source can be a laser and the light guide can be an optical fiber. In certain embodiments, the catheter system can also an inflatable balloon that encircles the distal tip of the light guide. The plasma target can be positioned within the inflatable balloon.

(Continued)

The target gap distance can be greater than 1 µm. The plasma target can have a target face that receives the light energy from the light guide. The target face can be angled relative to a direction the light energy is emitted to the plasma target. The plasma target can be formed from one or more of tungsten, tantalum, platinum, molybdenum, niobium, iridium, magnesium oxide, beryllium oxide, tungsten carbide, titanium nitride, titanium carbonitride and titanium carbide.

30 Claims, 15 Drawing Sheets

(51) Int. Cl.
*A61B 1/00* (2006.01)
*A61B 5/027* (2006.01)
*A61B 17/00* (2006.01)

(56) References Cited

U.S. PATENT DOCUMENTS

| | | | |
|---|---|---|---|
| 4,799,479 | A | 1/1989 | Spears |
| 4,913,142 | A | 4/1990 | Kittrell et al. |
| 4,955,895 | A | 9/1990 | Sugiyama |
| 4,960,108 | A | 10/1990 | Reichel et al. |
| 4,994,059 | A | 2/1991 | Kosa et al. |
| 5,034,010 | A | 7/1991 | Kittrell et al. |
| 5,041,121 | A | 8/1991 | Wondrazek et al. |
| 5,104,391 | A | 4/1992 | Ingle |
| 5,116,227 | A | 5/1992 | Levy |
| 5,152,768 | A | 10/1992 | Bhatta |
| 5,173,049 | A | 12/1992 | Levy |
| 5,181,921 | A | 1/1993 | Makita et al. |
| 5,200,838 | A | 4/1993 | Nudelman |
| 5,290,277 | A | 3/1994 | Vercimak et al. |
| 5,372,138 | A | 12/1994 | Crowley |
| 5,400,428 | A | 3/1995 | Grace |
| 5,422,926 | A * | 6/1995 | Smith .................... A61B 90/11 378/138 |
| 5,454,809 | A | 10/1995 | Janssen |
| 5,509,917 | A | 4/1996 | Cecchetti |
| 5,540,679 | A | 7/1996 | Fram |
| 5,562,657 | A | 10/1996 | Griffin |
| 5,598,494 | A | 1/1997 | Behrmann et al. |
| 5,609,606 | A | 3/1997 | O'Boyle |
| 5,611,807 | A | 3/1997 | O'Boyle |
| 5,697,377 | A | 12/1997 | Wittkampf |
| 5,718,241 | A | 2/1998 | Ben-Haim et al. |
| 5,729,583 | A * | 3/1998 | Tang ..................... H01J 35/32 378/138 |
| 5,772,609 | A | 6/1998 | Nguyen et al. |
| 5,891,135 | A | 4/1999 | Jackson et al. |
| 5,906,611 | A | 5/1999 | Dodick et al. |
| 5,944,687 | A | 8/1999 | Benett et al. |
| 6,080,119 | A | 6/2000 | Schwarze et al. |
| 6,123,923 | A | 9/2000 | Unger |
| 6,139,510 | A | 10/2000 | Palermo |
| 6,186,963 | B1 | 2/2001 | Schwarze et al. |
| 6,203,537 | B1 | 3/2001 | Adrian |
| 6,210,404 | B1 | 4/2001 | Shadduck |
| 6,339,470 | B1 | 1/2002 | Papademetriou et al. |
| 6,368,318 | B1 | 4/2002 | Visuri et al. |
| 6,500,174 | B1 | 12/2002 | Maguire et al. |
| 6,514,203 | B2 | 2/2003 | Bukshpan |
| 6,514,249 | B1 | 2/2003 | Maguire |
| 6,524,251 | B2 | 3/2003 | Rabiner et al. |
| 6,538,739 | B1 | 3/2003 | Visuri et al. |
| 6,607,502 | B1 | 8/2003 | Maguire et al. |
| 6,652,547 | B2 | 11/2003 | Rabiner et al. |
| 6,666,834 | B2 | 12/2003 | Restle et al. |
| 6,773,447 | B2 | 8/2004 | Laguna |
| 6,849,994 | B1 | 2/2005 | White et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,309,324 | B2 | 12/2007 | Hayes et al. |
| 7,470,240 | B2 | 12/2008 | Schultheiss et al. |
| 7,569,032 | B2 | 8/2009 | Naimark et al. |
| 7,599,588 | B2 | 10/2009 | Eberle et al. |
| 7,713,260 | B2 | 5/2010 | Lessard |
| 7,758,572 | B2 | 7/2010 | Weber et al. |
| 7,810,395 | B2 | 10/2010 | Zhou |
| 7,850,685 | B2 | 12/2010 | Kunis et al. |
| 7,867,178 | B2 | 1/2011 | Simnacher |
| 7,972,299 | B2 | 7/2011 | Carter |
| 7,985,189 | B1 | 7/2011 | Ogden et al. |
| 8,162,859 | B2 | 4/2012 | Schultheiss et al. |
| 8,166,825 | B2 | 5/2012 | Zhou |
| 8,192,368 | B2 | 6/2012 | Woodruff |
| 8,292,913 | B2 | 10/2012 | Warnack |
| 8,364,235 | B2 | 1/2013 | Kordis et al. |
| 8,419,613 | B2 | 4/2013 | Saadat |
| 8,439,890 | B2 | 5/2013 | Beyar |
| 8,556,813 | B2 | 10/2013 | Cashman et al. |
| 8,574,247 | B2 | 11/2013 | Adams et al. |
| 8,657,814 | B2 | 2/2014 | Werneth |
| 8,709,075 | B2 | 4/2014 | Adams et al. |
| 8,728,091 | B2 | 5/2014 | Hakala et al. |
| 8,747,416 | B2 | 6/2014 | Hakala et al. |
| 8,888,788 | B2 | 11/2014 | Hakala et al. |
| 8,956,371 | B2 | 2/2015 | Hawkins et al. |
| 8,956,374 | B2 | 2/2015 | Hawkins et al. |
| 8,986,339 | B2 | 3/2015 | Warnack |
| 8,992,817 | B2 | 3/2015 | Stamberg |
| 9,005,216 | B2 | 4/2015 | Hakala et al. |
| 9,011,462 | B2 | 4/2015 | Adams et al. |
| 9,011,463 | B2 | 4/2015 | Adams et al. |
| 9,044,618 | B2 | 6/2015 | Hawkins et al. |
| 9,044,619 | B2 | 6/2015 | Hawkins et al. |
| 9,072,534 | B2 | 7/2015 | Adams et al. |
| 9,131,949 | B2 | 9/2015 | Coleman et al. |
| 9,138,249 | B2 | 9/2015 | Adams et al. |
| 9,138,260 | B2 | 9/2015 | Miller et al. |
| 9,180,280 | B2 | 11/2015 | Hawkins et al. |
| 9,220,521 | B2 | 12/2015 | Hawkins et al. |
| 9,237,984 | B2 | 1/2016 | Hawkins et al. |
| 9,289,132 | B2 | 3/2016 | Ghaffari et al. |
| 9,289,224 | B2 | 3/2016 | Adams et al. |
| 9,320,530 | B2 | 4/2016 | Grace |
| 9,333,000 | B2 | 5/2016 | Hakala et al. |
| 9,375,223 | B2 | 6/2016 | Wallace |
| 9,421,025 | B2 | 8/2016 | Hawkins et al. |
| 9,433,428 | B2 | 9/2016 | Hakala et al. |
| 9,504,809 | B2 | 11/2016 | Bo |
| 9,510,887 | B2 | 12/2016 | Burnett |
| 9,522,012 | B2 | 12/2016 | Adams |
| 9,554,815 | B2 | 1/2017 | Adams et al. |
| 9,555,267 | B2 | 1/2017 | Ein-gal |
| 9,566,209 | B2 | 2/2017 | Katragadda et al. |
| 9,579,114 | B2 | 2/2017 | Mantell et al. |
| 9,629,567 | B2 | 4/2017 | Porath et al. |
| 9,642,673 | B2 | 5/2017 | Adams |
| 9,662,069 | B2 | 5/2017 | De Graff et al. |
| 9,687,166 | B2 | 6/2017 | Subramaniam |
| 9,730,715 | B2 | 8/2017 | Adams |
| 9,764,142 | B2 | 9/2017 | Imran |
| 9,814,476 | B2 | 11/2017 | Adams et al. |
| 9,861,377 | B2 | 1/2018 | Mantell et al. |
| 9,867,629 | B2 | 1/2018 | Hawkins et al. |
| 9,894,756 | B2 | 2/2018 | Weinkam et al. |
| 9,955,946 | B2 | 5/2018 | Miller et al. |
| 9,974,963 | B2 | 5/2018 | Imran |
| 9,974,970 | B2 | 5/2018 | Nuta et al. |
| 9,993,292 | B2 | 6/2018 | Adams et al. |
| 10,039,561 | B2 | 8/2018 | Adams et al. |
| 10,136,829 | B2 | 11/2018 | Deno et al. |
| 10,149,690 | B2 | 12/2018 | Hawkins et al. |
| 10,159,505 | B2 | 12/2018 | Hakala et al. |
| 10,194,994 | B2 | 2/2019 | Deno et al. |
| 10,201,387 | B2 | 2/2019 | Grace et al. |
| 10,206,698 | B2 | 2/2019 | Hakala et al. |
| 10,226,265 | B2 | 3/2019 | Ku et al. |

(56) References Cited

U.S. PATENT DOCUMENTS

| | | |
|---|---|---|
| 10,357,264 B2 | 7/2019 | Kat-Kuoy |
| 10,405,923 B2 | 9/2019 | Yu et al. |
| 10,406,031 B2 | 9/2019 | Thyzel |
| 10,420,569 B2 | 9/2019 | Adams |
| 10,441,300 B2 | 10/2019 | Hawkins |
| 10,478,202 B2 | 11/2019 | Adams et al. |
| 10,517,620 B2 | 12/2019 | Adams |
| 10,517,621 B1 | 12/2019 | Hakala et al. |
| 10,537,287 B2 | 1/2020 | Braido et al. |
| 10,555,744 B2 | 2/2020 | Nguyen et al. |
| 10,561,428 B2 | 2/2020 | Eggert et al. |
| 10,646,240 B2 | 5/2020 | Betelia et al. |
| 10,682,178 B2 | 6/2020 | Adams et al. |
| 10,702,293 B2 | 7/2020 | Adams et al. |
| 10,709,462 B2 | 7/2020 | Nguyen et al. |
| 10,758,255 B2 | 9/2020 | Adams |
| 10,842,567 B2 | 11/2020 | Grace et al. |
| 10,959,743 B2 | 3/2021 | Adams et al. |
| 10,966,737 B2 | 4/2021 | Nguyen |
| 10,967,156 B2 | 4/2021 | Gulachenski |
| 10,973,538 B2 | 4/2021 | Hakala et al. |
| 11,000,299 B2 | 5/2021 | Hawkins et al. |
| 11,020,135 B1 | 6/2021 | Hawkins |
| 11,026,707 B2 | 6/2021 | Ku et al. |
| 11,058,492 B2 | 7/2021 | Grace et al. |
| 11,076,874 B2 | 8/2021 | Hakala et al. |
| 11,213,661 B2 | 1/2022 | Spindler |
| 11,229,772 B2 | 1/2022 | Nita |
| 11,229,776 B2 | 1/2022 | Kugler et al. |
| 11,246,659 B2 | 2/2022 | Grace et al. |
| 2001/0051784 A1 | 12/2001 | Brisken |
| 2002/0045811 A1 | 4/2002 | Kittrell et al. |
| 2002/0065512 A1 | 5/2002 | Fjield et al. |
| 2002/0082553 A1 | 6/2002 | Duchamp |
| 2002/0183729 A1 | 12/2002 | Farr et al. |
| 2002/0188204 A1 | 12/2002 | McNamara et al. |
| 2003/0009157 A1 | 1/2003 | Levine et al. |
| 2003/0050632 A1 | 3/2003 | Fjield et al. |
| 2003/0065316 A1 | 4/2003 | Levine et al. |
| 2003/0114901 A1 | 6/2003 | Loeb et al. |
| 2003/0176873 A1 | 9/2003 | Chernenko et al. |
| 2004/0002677 A1 | 1/2004 | Gentsler |
| 2004/0073251 A1 | 4/2004 | Weber |
| 2004/0097996 A1 | 5/2004 | Rabiner |
| 2004/0133254 A1 | 7/2004 | Sterzer et al. |
| 2004/0162508 A1 | 8/2004 | Uebelacker |
| 2004/0243119 A1 | 12/2004 | Lane et al. |
| 2004/0249401 A1 | 12/2004 | Rabiner |
| 2005/0010095 A1 | 1/2005 | Stewart et al. |
| 2005/0021013 A1 | 1/2005 | Visuri |
| 2005/0080396 A1 | 4/2005 | Rontal |
| 2005/0113722 A1 | 5/2005 | Schultheiss |
| 2005/0171437 A1 | 8/2005 | Carberry |
| 2005/0171527 A1 | 8/2005 | Bhola |
| 2005/0251131 A1 | 11/2005 | Lesh |
| 2005/0273014 A1 | 12/2005 | Gianchandani et al. |
| 2005/0277839 A1 | 12/2005 | Alderman et al. |
| 2006/0033241 A1 | 2/2006 | Schewe et al. |
| 2006/0084966 A1 | 4/2006 | Maguire et al. |
| 2006/0190022 A1 | 8/2006 | Beyar et al. |
| 2006/0200039 A1 | 9/2006 | Brockway et al. |
| 2006/0221528 A1 | 10/2006 | Li et al. |
| 2006/0241524 A1 | 10/2006 | Lee et al. |
| 2006/0241572 A1 | 10/2006 | Zhou |
| 2006/0241733 A1 | 10/2006 | Zhang et al. |
| 2006/0270976 A1 | 11/2006 | Savage et al. |
| 2007/0060990 A1 | 3/2007 | Satake |
| 2007/0088380 A1 | 4/2007 | Hirszowicz et al. |
| 2007/0118057 A1 | 5/2007 | Ein-gal |
| 2007/0142819 A1 | 6/2007 | El-Nounou et al. |
| 2007/0179496 A1 | 8/2007 | Swoyer |
| 2007/0239082 A1 | 10/2007 | Schultheiss et al. |
| 2007/0255270 A1 | 11/2007 | Carney |
| 2007/0264353 A1 | 11/2007 | Myntti et al. |
| 2007/0270897 A1 | 11/2007 | Skerven |
| 2007/0299392 A1 | 12/2007 | Beyar et al. |
| 2008/0086118 A1 | 4/2008 | Lai |
| 2008/0095714 A1 | 4/2008 | Castella et al. |
| 2008/0097251 A1 | 4/2008 | Babaev |
| 2008/0108867 A1 | 5/2008 | Zhou |
| 2008/0114341 A1 | 5/2008 | Thyzel |
| 2008/0132810 A1 | 6/2008 | Scoseria et al. |
| 2008/0195088 A1 | 8/2008 | Farr et al. |
| 2008/0214891 A1 | 9/2008 | Slenker et al. |
| 2008/0296152 A1 | 12/2008 | Voss |
| 2008/0319356 A1 | 12/2008 | Cain et al. |
| 2009/0036803 A1 | 2/2009 | Warlick et al. |
| 2009/0043300 A1 | 2/2009 | Reitmajer et al. |
| 2009/0054881 A1 | 2/2009 | Krespi |
| 2009/0097806 A1 | 4/2009 | Viellerobe et al. |
| 2009/0125007 A1 | 5/2009 | Splinter |
| 2009/0192495 A1 | 7/2009 | Ostrovsky et al. |
| 2009/0247945 A1 | 10/2009 | Levit |
| 2009/0299327 A1 | 12/2009 | Tilson et al. |
| 2009/0306533 A1 | 12/2009 | Rousche |
| 2009/0312768 A1 | 12/2009 | Hawkins et al. |
| 2010/0016862 A1 | 1/2010 | Hawkins et al. |
| 2010/0036294 A1 | 2/2010 | Mantell et al. |
| 2010/0114020 A1 | 5/2010 | Hawkins et al. |
| 2010/0114065 A1 | 5/2010 | Hawkins et al. |
| 2010/0125268 A1 | 5/2010 | Gustus et al. |
| 2010/0160903 A1 | 6/2010 | Krespi |
| 2010/0168572 A1 | 7/2010 | Sliwa |
| 2010/0179632 A1 | 7/2010 | Bruszewski et al. |
| 2010/0191089 A1 | 7/2010 | Stebler et al. |
| 2010/0198114 A1 | 8/2010 | Novak et al. |
| 2010/0199773 A1 | 8/2010 | Zhou |
| 2010/0222786 A1 | 9/2010 | Kassab |
| 2010/0234875 A1 | 9/2010 | Allex et al. |
| 2010/0256535 A1 | 10/2010 | Novak et al. |
| 2011/0034832 A1 | 2/2011 | Cioanta et al. |
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0157892 A1 | 6/2012 | Reitmajer et al. |
| 2012/0197245 A1 | 8/2012 | Burnett |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0116714 A1 | 5/2013 | Adams et al. |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0345617 A1 | 12/2013 | Wallace |
| 2014/0005576 A1 | 1/2014 | Adams |

(56) References Cited

U.S. PATENT DOCUMENTS

| | | |
|---|---|---|
| 2014/0005706 A1 | 1/2014 | Gelfand et al. |
| 2014/0012186 A1 | 1/2014 | Thyzel |
| 2014/0039002 A1 | 1/2014 | Adams et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0114198 A1 | 4/2014 | Samada et al. |
| 2014/0153087 A1 | 6/2014 | Hutchings et al. |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0336632 A1 | 11/2014 | Toth |
| 2015/0005576 A1 | 1/2015 | Diodone et al. |
| 2015/0039002 A1 | 2/2015 | Hawkins |
| 2015/0073430 A1 | 3/2015 | Hakala et al. |
| 2015/0080875 A1 | 3/2015 | Kasprzyk et al. |
| 2015/0105715 A1 | 4/2015 | Pikus et al. |
| 2015/0119870 A1 | 4/2015 | Rudie |
| 2015/0141764 A1 | 5/2015 | Harks et al. |
| 2015/0250542 A1 | 9/2015 | Islam |
| 2015/0276689 A1 | 10/2015 | Watanabe |
| 2015/0313732 A1 | 11/2015 | Fulton, III |
| 2015/0359432 A1 | 12/2015 | Ehrenreich |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0143522 A1 | 5/2016 | Ransbury |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184570 A1 | 6/2016 | Grace et al. |
| 2016/0262784 A1 | 9/2016 | Grace et al. |
| 2016/0270806 A1 | 9/2016 | Wallace |
| 2016/0234534 A1 | 11/2016 | Hawkins et al. |
| 2016/0324564 A1 | 11/2016 | Gerlach et al. |
| 2016/0331389 A1 | 11/2016 | Hakala et al. |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0056087 A1 | 3/2017 | Buckley |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0049877 A1 | 2/2018 | Venkatasubramanian |
| 2018/0092763 A1 | 4/2018 | Dagan et al. |
| 2018/0098779 A1 | 4/2018 | Betelia et al. |
| 2018/0152568 A1 | 6/2018 | Kat-kuoy |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |
| 2018/0304053 A1 | 10/2018 | Eggert et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0099588 A1 | 4/2019 | Ramanath et al. |
| 2019/0104933 A1 | 4/2019 | Stern |
| 2019/0150960 A1 | 5/2019 | Nguyen et al. |
| 2019/0175111 A1 | 6/2019 | Genereux et al. |
| 2019/0175300 A1 | 6/2019 | Horn |
| 2019/0175372 A1 | 6/2019 | Boydan et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0282249 A1 | 9/2019 | Tran et al. |
| 2019/0282250 A1 | 9/2019 | Tran et al. |
| 2019/0328259 A1 | 10/2019 | Deno et al. |
| 2019/0365400 A1 | 12/2019 | Adams et al. |
| 2019/0388002 A1 | 12/2019 | Bozsak et al. |
| 2019/0388110 A1 | 12/2019 | Nguyen et al. |
| 2019/0388151 A1 | 12/2019 | Bhawalkar |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046949 A1 | 2/2020 | Chisena et al. |
| 2020/0054352 A1 | 2/2020 | Brouillette et al. |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0107960 A1 | 4/2020 | Bacher |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0383724 A1 | 12/2020 | Adams et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0128241 A1 | 5/2021 | Schultheis |
| 2021/0137598 A1 | 5/2021 | Cook |
| 2021/0153939 A1 | 5/2021 | Cook |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0307828 A1 | 10/2021 | Schultheis |
| 2021/0330384 A1 | 10/2021 | Cook |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |

(56) References Cited

U.S. PATENT DOCUMENTS

| | | |
|---|---|---|
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0273324 A1 | 9/2022 | Schultheis |
| 2022/0354578 A1 | 11/2022 | Cook |
| 2022/0387106 A1 | 12/2022 | Cook |
| 2023/0013920 A1 | 1/2023 | Massimini |

FOREIGN PATENT DOCUMENTS

| | | |
|---|---|---|
| CA | 2229806 | 3/1997 |
| CA | 2983655 | 10/2016 |
| CN | 102057422 | 5/2011 |
| CN | 109223100 | 1/2019 |
| CN | 110638501 A | 1/2020 |
| CN | 11399346 | 1/2022 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| DE | 3038445 A1 | 5/1982 |
| DE | 3836337 A | 4/1990 |
| DE | 3913027 A1 | 10/1990 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 1179993 A1 | 2/2002 |
| EP | 1946712 | 7/2008 |
| EP | 1946712 A1 | 7/2008 |
| EP | 2157569 | 2/2010 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3318204 | 5/2018 |
| EP | 3461438 A1 | 4/2019 |
| EP | 3473195 A1 | 4/2019 |
| EP | 3643260 A1 | 4/2020 |
| EP | 3076881 B1 | 1/2022 |
| EP | 3932342 | 1/2022 |
| EP | 3936140 | 1/2022 |
| EP | 4051154 | 9/2022 |
| GB | 1082397 | 9/1967 |
| JP | S62275446 A | 11/1987 |
| KR | 20050098932 | 10/2005 |
| KR | 20080040111 | 5/2008 |
| KR | 20160090877 A | 8/2016 |
| WO | WO9007904 A1 | 7/1990 |
| WO | WO9105332 A1 | 4/1991 |
| WO | 9203095 A1 | 3/1992 |
| WO | 1992008515 A2 | 5/1992 |
| WO | 9902095 A1 | 1/1999 |
| WO | 9920189 A1 | 4/1999 |
| WO | WO200067648 | 11/2000 |
| WO | WO2000067648 A1 | 11/2000 |
| WO | 2001003599 A1 | 1/2001 |
| WO | 2006006169 A2 | 1/2006 |
| WO | WO2009121017 | 10/2009 |
| WO | WO2009149321 A1 | 12/2009 |
| WO | 2010042653 A1 | 4/2010 |
| WO | WO2011094379 | 8/2011 |
| WO | 2011126580 A2 | 10/2011 |
| WO | WO2012025833 | 3/2012 |
| WO | WO20120052924 A1 | 4/2012 |
| WO | WO2012099974 A2 | 7/2012 |
| WO | WO20120120495 A2 | 9/2012 |
| WO | WO2013119662 | 8/2013 |
| WO | 20130169807 A1 | 11/2013 |
| WO | WO2014022436 A1 | 2/2014 |
| WO | WO2014025397 A1 | 2/2014 |
| WO | WO20140022867 A1 | 2/2014 |
| WO | WO2014138582 | 9/2014 |
| WO | WO2015056662 | 4/2015 |
| WO | WO2015097251 A2 | 7/2015 |
| WO | 2015177790 A1 | 11/2015 |
| WO | WO2016089683 | 6/2016 |
| WO | WO2016090175 | 6/2016 |
| WO | WO2016109739 | 7/2016 |
| WO | WO2016151595 A1 | 9/2016 |
| WO | WO2017004432 A1 | 1/2017 |
| WO | WO20170192869 A1 | 11/2017 |
| WO | 20180022641 A1 | 2/2018 |
| WO | WO2018022593 A1 | 2/2018 |
| WO | WO2018083666 | 5/2018 |
| WO | 2018175322 A1 | 9/2018 |
| WO | WO2019200201 A1 | 10/2019 |
| WO | WO2019215869 A1 | 11/2019 |
| WO | WO2019222843 | 11/2019 |
| WO | WO2020056031 | 3/2020 |
| WO | WO20200086361 A1 | 4/2020 |
| WO | WO2020089876 A1 | 5/2020 |
| WO | WO2020256898 | 12/2020 |
| WO | WO2020256898 A1 | 12/2020 |
| WO | WO2020256949 | 12/2020 |
| WO | WO2020256949 A1 | 12/2020 |
| WO | WO2020263469 A1 | 12/2020 |
| WO | WO2020263685 A1 | 12/2020 |
| WO | WO2020263687 A1 | 12/2020 |
| WO | WO2020263688 A1 | 12/2020 |
| WO | WO2020263689 A1 | 12/2020 |
| WO | WO2021067563 | 4/2021 |
| WO | 2021086571 A1 | 5/2021 |
| WO | 2021101766 A1 | 5/2021 |
| WO | WO2021096922 A1 | 5/2021 |
| WO | WO2021126762 A1 | 6/2021 |
| WO | WO2021162855 A1 | 8/2021 |
| WO | WO2021173417 A1 | 9/2021 |
| WO | WO2021183367 A1 | 9/2021 |
| WO | WO2021183401 A1 | 9/2021 |
| WO | WO2021188233 A1 | 9/2021 |
| WO | WO2021202248 A1 | 10/2021 |

(56) References Cited

FOREIGN PATENT DOCUMENTS

| | | |
|---|---|---|
| WO | WO2021231178 A1 | 11/2021 |
| WO | WO2021247685 A1 | 12/2021 |
| WO | WO2021257425 A1 | 12/2021 |
| WO | WO2022007490 | 1/2022 |
| WO | WO2022008440 | 1/2022 |
| WO | WO2022010767 A1 | 1/2022 |
| WO | WO2022055784 | 3/2022 |
| WO | WO2022125525 | 6/2022 |
| WO | WO2022154954 | 7/2022 |
| WO | WO2022173719 | 8/2022 |
| WO | WO2022187058 | 9/2022 |
| WO | WO2022216488 | 10/2022 |
| WO | WO2022240674 | 11/2022 |
| WO | WO2022260932 | 12/2022 |

OTHER PUBLICATIONS

Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.

Nademanee, Koonlawee, et al. "A new approach for catheter ablation of atrial fibrillation: mapping of the electrophysiologic substrate." Journal of the American College of Cardiology 43.11 (2004): 2044-2053.

Calkins, Hugh "Three dimensional mapping of atrial fibrillation: techniques and necessity." Journal of interventional cardiac electrophysiology 13.1 (2005): 53-59.

Shariat, Mohammad Hassan. Processing the intracardiac electrogram for atrial fibrillation ablation Diss. Queen's University (Canada), 2016.

Meng et al., "Accurate Recovery of Atrial Endocardial Potential Maps From Non-contact Electrode Data." Auckland Bioengineering Institute. (ID 1421).

Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368).

Sacher et al., "Comparison of Manual Vs Automatic Annotation to Identify Abnormal Substrate for Scar Related VT Ablation." LIRYC Institute, Bordeaux University Hospital, France (ID 1336).

Oriel Instruments, "Introduction to Beam Splitters for Optical Research Applications", Apr. 2014, pp. 1-9, https://www.azoptics.com/Article.aspx?ArticaID=871.

International Search Report and Written Opinion dated Apr. 12, 2021 in PCT Application Serial No. PCT/US2020/059960.

International Search Report and Written Opinion dated Apr. 13, 2021 in PCT Application Serial No. PCT/US2020/064846.

International Search Report and Written Opinion dated Apr. 13, 2021 in PCT Application Serial No. PCT/US2021/013944.

International Search Report and Written Opinion dated May 25, 2021 in PCT Application Serial No. PCT/US2021/017604.

Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.

Jones, H. M., et al. "Pulsed dielectric breakdown of pressurized water and salt solutions", Journal of Applied Physics, Jun. 1998, pp. 795-805, vol. 77, No. 2, American Institute of Physics.

Kozulin, I., et al. "The dynamic of the water explosive vaporization on the flat microheater", Journal of Physics: Conference Series, 2018, pp. 1-4, IOP Publishing, Russia.

Cross, F., "Laser Angioplasty", Vascular Medicine Review, 1992, pp. 21-30, Edward Arnold.

Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales Calculation of Thresholds, Absorption Coefficients, and Energy Density", IEEE Journal of Quantum Electronics, 1999, pp. 1156-1167, vol. 35, No. 8, IEEE.

Pratsos, A., "The use of Laser for the treatment of coronary artery disease", Bryn Mawr Hospital, 2010.

Li, Xian-Dong, et al. "Influence of deposited energy on shock wave induced by underwater pulsed current discharge", Physics of Plasmas, 2016, vol. 23, American Institute of Physics.

Logunov, S., et al. "Light diffusing optical fiber illumination", Renewable Energy and the Environment Congress, 2013, Corning, NY, USA.

Maxwell, A. D., et al. "Cavitation clouds created by shock scattering from bubbles during histotripsy", Acoustical Society of America, 2011, pp. 1888-1898, vol. 130, No. 4, Acoustical Society of America.

Mcateer, James A., et al. "Ultracal-30 Gypsum Ailincial Stones for Research on the Mechinisms of Stone Breakage in Shock Wave Lithotripsy", 2005, pp. 429-434, Springer-Verlag.

Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.

Vogel, A., et al. "Mechanisms of Pulsed Laser Ablation of Biological Tissues", Chemical Reviews, 2003, pp. 577-644, vol. 103, No. 2, American Chemical Society.

Medlight, "Cylindrical light diffuser Model RD-ML", Medlight S.A., Switzerland.

Medlight, "Cylindircal light diffuser Model RD", Medlight S.A., Switzerland.

Mayo, Michael E., "Interaction of Laser Radiation with Urinary Calculi", Cranfield University Defense and Security, PhD Thesis, 2009, Cranfield University.

Vogel, A., et al. "Minimization of Cavitation Effects in Pulsed Laser Ablation Illustrated on Laser Angioplasty", Applied Physics, 1996, pp. 173-182, vol. 62, Springer-Verlag.

Mirshekari, G., et al. "Microscale Shock Tube", Journal of Microelectromechanical Systems, 2012, pp. 739-747, vol. 21, No. 3, IEEE.

"Polymicro Sculpted Silica Fiber Tips", Molex, 2013, Molex.

Zhou, J., et al. "Optical Fiber Tips and Their Applications", Polymicro Technologies A Subsidiary of Molex, Nov. 2007.

Liang, Xiao-Xuan, et al. "Multi-Rate-Equation modeling of the energy spectrum of laser-induced conduction band electrons in water", Optics Express, 2019, vol. 27, No. 4, Optical Society of America.

Nachabe, R., et al. "Diagnosis of breast cancer using diffuse optical spectroscopy from 500 to 1600 nm: comparison of classification methods", Journal of Biomedical Optics, 2011, vol. 16(8), SPIE.

Naugol'Nykh, K. A., et al. "Spark Discharges in Water", Academy of Sciences USSR Institute of Acoustics, 1971, Nauka Publishing Co., Moscow, USSR.

Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.

Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.

Ohl, Siew-Wan, et al. "Bubbles with shock waves and ultrasound: a review", Interface Focus, pp. 1-15, vol. 5, The Royal Society Publishing.

Zheng, W., "Optical Lenses Manufactured on Fiber Ends", IEEE, 2015, Splicer Engineering, Duncan SC USA.

Dwyer, P.J., et al. "Optically integrating balloon device for photodynamic therapy", Lasers in Surgery and Medicine, 2000, pp. 58-66, vol. 26, Issue 1, Wiley-Liss Inc., Boston MA USA.

"The New Optiguide DCYL700 Fiber Optic Diffuser Series", Optiguide Fiber Optic Spec Sheet, Pinnacle Biologies, 2014, Pinnacle Biologies, Illinois, USA.

Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.

(56) References Cited

OTHER PUBLICATIONS

Oshita, D., et al. "Characteristic of Cavitation Bubbles and Shock Waves Generated by Pulsed Electric Discharges with Different Voltages", IEEE, 2012, pp. 102-105, Kumamoto, Japan.

Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.

Murray, A., et al. "Peripheral laser angioplasty with pulsed dye laser and ball tipped optical fibres", The Lancet, 1989, pp. 1471-1474, vol. 2, Issue 8678-8679.

Mohammadzadeh, M., et al. "Photoacoustic Shock Wave Emission and Cavitation from Structured Optical Fiber Tips", Applied Physics Letters, 2016, vol. 108, American Institute of Physics Publishing LLC.

Doukas, A. G., et al. "Physical characteristics and biological effects of laser-induced stress waves", Ultrasound in Medicine and Biology, 1996, pp. 151-164, vol. 22, Issue 2, World Federation for Ultrasound in Medicine and Biology, USA.

Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.

Piedrahita, Francisco S., "Experimental Research Work on a Sub-Millimeter Spark-Gap for Sub Nanosecond Gas Breakdown", Thesis for Universidad Nacional De Colombia, 2012, Bogota, Colombia.

Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 398-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedical Optics, 2011, pp. 1-10, vol. 16, No. 1, SPIE.

Serruys, P.W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissipation After Laser-induced Breakdown", SPIE, 1998, pp. 180-189, vol. 3254, SPIE.

International Search Report and Written Opinion dated Nov. 8, 2022 in PCT Application Serial No. PCTUS/2022/039678.

International Search Report and Written Opinion dated Sep. 14, 2020 in PCT Application Serial No. PCT/US2020/038523.

International Search Report and Written Opinion dated Oct. 2, 2020 in PCT Application Serial No. PCT/US2020/036107.

International Search Report and Written Opinion dated Sep. 11, 2020 in PCT Application Serial No. PCT/US2020038517.

International Search Report and Written Opinion dated Sep. 9, 2020 in PCT Application Serial No. PCT/US2020038530.

International Search Report and Written Opinion dated Sep. 11, 2020 in PCT Application Serial No. PCT/US2020038521.

International Search Report and Written Opinion dated Sep. 7, 2020 in PCT Application Serial No. PCT/US2020034642.

International Preliminary Report on Patentability dated Sep. 15, 2020 in PCT Application Serial No. PCT/US2019/022009.

Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26.

Chen, Sung-Liang, "Review of Laser-Generated Ultrasound Transmitters and their Applications to All-Optical Ultrasound Transducers and Imaging", Appl. Sci 2017, 7, 25.

Colchester, R., et al. "Laser-Generated ultrasound with optica fibres using functionalised carbon nanotube composite coatings", Appl. Phys. Lett., 2014, vol. 104, 173504.

Poduval, R., et al. "Optical fiber ultrasound transmitter with electrospun carbon nanotube-polymer composite", Appl. Phys. Lett, 2017, vol. 110, 223701.

Tian, J., et al. "Distributed fiber-optic laser-ultrasound generation based on ghost-mode of tilted fiber Bragg gratings", Optical Society of America, 2013.

Kim, J., et al. "Optical Fiber Laser-Generated-Focused-Ultrasound Transducers for Intravascular Therapies", IEEE, 2017.

Kang, H., et al. "Enhanced photocoagulation with catheter-based diffusing optical device", Journal of Biomedical Optics, 2012, vol. 17, Issue 11, 118001.

International Search Report and Written Opinion dated Jan. 3, 2020, in PCT Application Serial No. PCT/US2019/056579.

Communication Pursuant to Article 94(3) EPC, for European Patent Application No. 18185152.8, dated Jan. 16, 2019.

European Search Report, for European Patent Application No. 18185152.8, dated Dec. 20, 2018.

Schafter+Kirchhoff, Laser Beam Couplers series 60SMS for coupling into single-mode and polarization-maintaining fiber cables, Schafter+Kirchhoff, pp. 1-5, Germany.

International Search Report and Written Opinion dated Jan. 29, 2020 in PCT Application Serial No. PCT/US2020/059961.

International Search Report and Written Opinion dated Jan. 20, 2020 in PCT Application Serial No. PCT/US2020/054792.

International Search Report and Written Opinion dated Feb. 19, 2021 in PCT Application Serial No. PCT/US2020/059960.

International Search Report and Written Opinion, issued by the EP/ISA, in PCT/US2021/048819, dated Jan. 14, 2022.

International Search Report and Written Opinion dated Jun. 28, 2022, in PCT Application Serial No. PCT/US2022/015577.

International Search Report and Written Opinion dated Jun. 27, 2022, in PCT Application Serial No. PCT/US2022/022460.

Medlight, "Cylindrical light diffuser Model RD-ML", Medlight S.A., Switzerland. 2015. This reference was cited in a prior Information Disclosure Statement. However, the relevant date was missing. The date has now been added.).

Medlight, "Cylindircal light diffuser Model RD", Medlight S.A., Switzerland. 2015. This reference was cited in a prior Information Disclosure Statement. However, the relevant date was missing. The date has now been added.).

Ohl, Siew-Wan, et al. "Bubbles with shock waves and ultrasound: a review", Interface Focus, pp. 1-15, vol. 5, The Royal Society Publishing Oct. 2015. This reference was cited in a prior Information Disclosure Statement. However, the relevant date was missing. The date has now been added.).

Schafter+Kirchhoff, Laser Beam Couplers series 60SMS for coupling into single-mode and polarizationmaintaining fiber cables, Schafter+Kirchhoff, pp. 1-5, Germany. Dec. 2, 2021. This reference

(56) References Cited

OTHER PUBLICATIONS was cited in a prior Information Disclosure Statement. However, the relevant date was missing. The date has now been added.).
Meng et al., "Accurate Recovery of Atrial Endocardial Potential Maps From Non-contact Electrode Data." Auckland Bioengineering Institute. (ID 1421). May 2019. This reference was cited in a prior Information Disclosure Statement. However, the relevant date was missing. The date has now been added.).
Jiang et al., "Multielectrode Catheter for Substrate Mapping for Scar-related VT Ablation: A Comparison Between Grid Versus Linear Configurations." UChicago Medicine, Center for Arrhythmia Care, Chicago IL (ID 1368). Posterior conference in San Francisco, May 8-11, 2019. This reference was cited in a prior Information Disclosure Statement. However, the relevant date was missing. The date has now been added.).
Sacher et al., "Comparison of Manual Vs Automatic Annotation to Identify Abnormal Substrate for Scar Related VT Ablation." LIRYC Institute, Bordeaux University Hospital, France (ID 1336). Poster for conference in San Francisco, May 8-11, 2019. This reference was cited in a prior Information Disclosure Statement. However, the relevant date was missing. The date has now been added.).
International Search Report and Written Opinion dated Jul. 29, 2020 in PCT Application Serial No. PCT/US2020/034005.
International Search Report and Written Opinion dated Aug. 25, 2022 in PCT Application Serial No. PCTUS/2022/028035.
International Search Report and Written Opinion dated Sep. 15, 2022 in PCT Application Serial No. PCTUS/2022/032045.
Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intiavascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.

Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.
Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.
Shangguan, HanQun et al. "Effects of Material Properties on Laser-induced Bubble Formation in Absorbing Liquids and on Submerged Targets", SPIE, 1997, pp. 783-791, vol. 2869.
Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser induced optical breakdown", Philips Research, 2013, The Netherlands.
Vogel, A. et al. "Energy balance of optical breakdown in water at nanosecond to femtosecond time scales", Applied Physics B 68, 1999, pp. 271-280, Springer-Verlag.
Kang, Hyun W., et al. "Enhanced photocoagulation with catheter based diffusing optical device", Journal of Biomedical Optics, Nov. 2012, vol. 17(11), SPIE.
Esch, E., et al. "A Simple Method for Fabricating Artificial Kidney Stones of Different Physical Properties", National Institute of Health Public Access Author Manuscript, Aug. 2010.

(56) References Cited

OTHER PUBLICATIONS

Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.
Nguyen, H., et al. "Fabrication of multipoint side-firing optical fiber by laser micro-ablation", Optics Letters, May 1, 2017, vol. 42, No. 9, Optical Society of America.
Zheng, W., "Optic Lenses Manufactured on Fiber Ends", 2015, IEEE, Duncan, SC, USA.
Whitesides, George M., et al. "Fluidic Optics", 2006, vol. 6329, SPIE, Cambridge, MA, USA.
Forero, M., et al. "Coronary lithoplasty: a novel treatment for stent underexpansion", Cardiovascular Flashlight, 2018, European Society of Cardiology.
Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/ US2022/015577.
International Search Report and Written Opinion dated May 13, 2022 in PCT Application Serial No. PCT/US2022/017562.
International Search Report and Written Opinion, issued by the European Patent Office for PCT/2021/XXX, dated Sep. 30, 2021.
Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds in Pure and Yb3 Doped Fused Silica", SPIE, 2007, pp. 6453171-64531712, vol. 6453, SPIE.
Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and on Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc , The Netherlands.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.

(56) References Cited

OTHER PUBLICATIONS

International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, dated Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
International Search Report and Written Opinion, PCT Application Serial No. PCT/US2022/047751 dated Feb. 10, 2023, by the European Patent Office.

* cited by examiner

PLASMA CREATION VIA NONAQUEOUS OPTICAL BREAKDOWN OF LASER PULSE ENERGY FOR BREAKUP OF VASCULAR CALCIUM

RELATED APPLICATIONS

This application claims priority on U.S. Provisional Application Ser. No. 62/863,506, filed on Jun. 19, 2019, and on U.S. Provisional Application Ser. No. 62/965,069, filed on Jan. 23, 2020. To the extent permitted, the contents of U.S. Provisional Application Ser. Nos. 62/863,506 and 62/965,069 are incorporated in their entirety herein by reference.

BACKGROUND

Vascular lesions within and adjacent to vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Creation of a plasma via optical breakdown of an aqueous solution requires a significant amount of energy in a short amount of time upon which it is converted into a therapeutic bubble and/or a therapeutic pressure wave. With sufficiently high energy and short pulse durations, there is potential to damage a distal end of a light guide used to deliver light energy to generate the plasma. A means to enhance the conversion efficiency of the light energy to (plasma) pressure wave and bubble growth would reduce the required power handling requirements of the optical delivery system. Therefore, less input energy would be required for an equivalent therapy while minimizing potential damage to the light guide.

Creation of the plasma near the distal end of a small diameter light guide as in the case of aqueous optical breakdown as one method for an intravascular lithotripsy catheter has the potential for self-damage due to its proximity to the plasma creation and/or the pressure wave, high plasma temperatures, and waterjet from collapse of the bubble, as non-exclusive examples.

SUMMARY

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

The present invention is directed toward a catheter system for treating a treatment site within or adjacent to a blood vessel. In certain embodiments, the catheter system includes a power source, a light guide and a plasma target. The light guide receives power from the power source. The light guide has a distal tip, and the light guide emits light energy in a direction away from the distal tip. The plasma target is spaced apart from the distal tip of the light guide by a target gap distance. The plasma target is configured to receive light energy from the light guide so that a plasma is generated at the plasma target upon receiving the light energy from the light guide.

In some embodiments, the power source is a laser. In various embodiments, the light guide is an optical fiber.

In certain embodiments, the catheter system can also include an inflatable balloon that encircles the distal tip of the light guide.

In various embodiments, the catheter system can also include an inflatable balloon. In some such embodiments, the plasma target can be positioned within the inflatable balloon.

In some embodiments, the target gap distance is greater than 1 µm, 10 µm, 100 µm, 1 mm, 2 mm, 3 mm, 5 mm and/or 1 cm.

In various embodiments, the plasma target can have a substantially circular cross-sectional configuration, a substantially square cross-sectional configuration, a substantially rectangular cross-sectional configuration, a substantially oval cross-sectional configuration, a substantially pentagonal cross-sectional configuration, a substantially hexagonal cross-sectional configuration, a substantially octagonal cross-sectional configuration, a polygonal cross-sectional configuration, a parallelogram cross-sectional configuration, a trapezoidal cross-sectional configuration or a substantially diamond-shaped cross-sectional configuration.

In certain embodiments, the catheter system can also include a guidewire lumen. In some such embodiments, the light guide can be coupled to the guidewire lumen.

In some embodiments, the plasma target has a target face that receives the light energy from the light guide. In various embodiments, the target face has an angle that is substantially orthogonal relative to a direction the light energy is emitted to the plasma target. In various embodiments, the target face has an angle that is greater than approximately 45 degrees and less than approximately 135 degrees relative to a direction the light energy is emitted to the plasma target. In certain embodiments, the target face can have an angle that is greater than zero degrees and less than 180 degrees relative to a direction the light energy is emitted to the plasma target.

In various embodiments, the light guide includes a distal region having a longitudinal axis. The direction the light energy is emitted can be substantially along the longitudinal axis of the distal region. Alternatively, the direction the light energy is emitted can be substantially perpendicular to the longitudinal axis of the distal region. Still alternatively, the direction the light energy is emitted can be angled relative to the longitudinal axis of the distal region. For example, in some embodiments, the direction the light energy is emitted has an angle relative to the longitudinal axis that is greater than zero degrees and less than 180 degrees. In various embodiments, the direction the light energy is emitted can have an angle relative to the longitudinal axis that is greater than 45 degrees and less than 135 degrees.

In certain embodiments, the catheter system can include a plurality of plasma targets that are spaced apart from the distal tip of the light guide. In some such embodiments, at least one of the plurality of plasma targets can be configured to receive light energy from the light guide.

In various embodiments, the plasma target can be at least partially formed from one of stainless steel and its variants, tungsten, tantalum, platinum, molybdenum, niobium, and iridium.

In some embodiments, the plasma target can be at least partially formed from one of magnesium oxide, beryllium oxide, tungsten carbide, titanium nitride, titanium carbonitride and titanium carbide.

In certain embodiments, the plasma target can be at least partially formed from one of diamond CVD and diamond.

In various embodiments, the plasma target can be at least partially formed from a transition metal, a metal alloy and/or a ceramic material.

In some embodiments, the plasma target can be fixedly coupled to the light guide. Alternatively, the plasma target can be movably coupled to the light guide. Still alternatively, the plasma target can be uncoupled from the light guide.

In some applications, the catheter system can include a guidewire lumen. In some such embodiments, the plasma target can substantially encircle the guidewire lumen.

In certain embodiments, the target face can include one or more surface features, which can include one or more of an indentation, a projection and a beveled edge.

In some embodiments, the target face can have a conical configuration, a pyramidal configuration, a dome-shaped configuration, a concave configuration, a convex configuration, a multi-faceted configuration, a coiled configuration, a spring-like configuration and/or a somewhat spiral configuration.

In various embodiments, the plasma target can be movable relative to the light guide. In some embodiments, the plasma target can be spring-loaded.

In certain embodiments, the catheter system can include a guidewire lumen, and the plasma target can be secured or otherwise coupled to the guidewire lumen.

In some embodiments, the catheter system can include a second light guide that receives power from the power source. The second light guide can have a second distal tip. The second light guide can emit light energy in a direction away from the second distal tip toward the plasma target. The plasma target can be spaced apart from the second distal tip of the second light guide. The plasma target can be configured to receive light energy from the second light guide so that a second plasma is generated at the plasma target upon receiving the light energy from the second light guide.

In certain embodiments, the catheter system can include a second light guide and a second plasma target. The second light guide can receive power from the power source. The second light guide can have a second distal tip. The second light guide can emit light energy in a direction away from the second distal tip toward the second plasma target. The second plasma target can be spaced apart from the plasma target and the second distal tip of the second light guide. The second plasma target can be configured to receive light energy from the second light guide so that a second plasma is generated at the second plasma target upon receiving the light energy from the second light guide.

In various embodiments, present invention can also be directed toward a method for creating plasma to optically break up vascular calcium in a blood vessel using laser pulse energy. In certain embodiments, the method includes the step of providing any one of the catheter systems shown and/or described herein.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
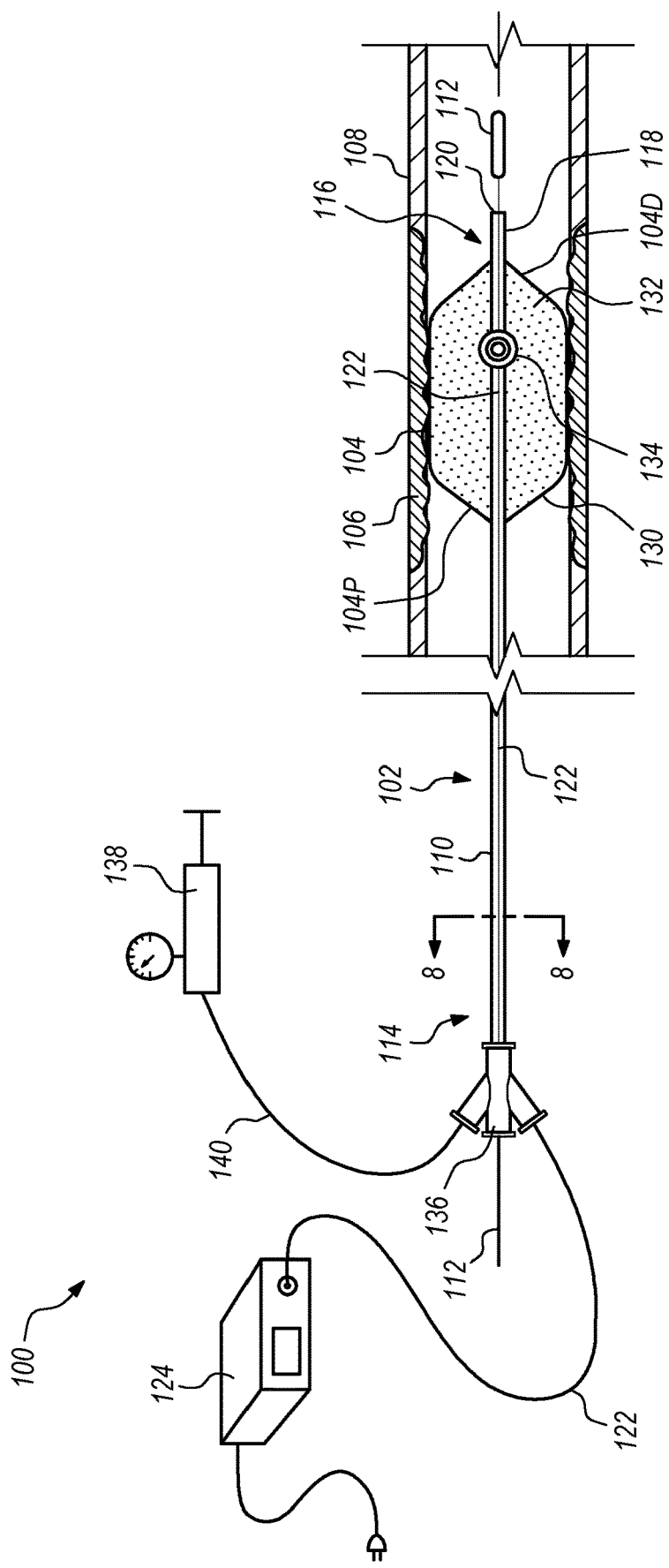
FIG. 1 is a schematic cross-sectional view of a catheter system having features of the present invention in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DESCRIPTION

Treatment of vascular lesions can reduce major adverse events or death in affected subjects. A major adverse event is one that can occur anywhere within the body due to the presence of a vascular lesion. Major adverse events can include, but are not limited to major adverse cardiac events, major adverse events in the peripheral or central vasculature, major adverse events in the brain, major adverse events in the musculature, or major adverse events in any of the internal organs.

In various embodiments, the systems and methods disclosed herein describe the use of a catheter systems including any number of light guides for generating pressure waves within an inflatable balloon (sometimes referred to herein simply as "balloon") for disrupting intervascular lesions. The catheter systems herein can utilize light energy to generate a plasma near the light guide disposed in the inflatable balloon located at or near a treatment site. As used herein, the treatment site can include a vascular lesion such as a calcified vascular lesion or a fibrous vascular lesion (hereinafter sometimes referred to simply as a "lesion"), typically found in a blood vessel and/or a heart valve. The plasma formation can initiate a pressure wave and can initiate the rapid formation of one or more bubbles that can rapidly expand to a maximum size and then dissipate through a cavitation event that can also launch a pressure wave upon collapse. The rapid expansion of the plasma-induced bubbles can generate one or more pressure waves within a balloon fluid and thereby impart pressure waves upon the treatment site. The pressure waves can transfer mechanical energy through an incompressible balloon fluid to a treatment site to impart a fracture force on the lesion. Without wishing to be bound by any particular theory, it is believed that the rapid change in balloon fluid momentum upon a balloon wall of the inflatable balloon that is in contact with or positioned near the lesion is transferred to the lesion to induce fractures in the lesion.

The catheter systems can include a catheter configured to advance to the lesion located within or adjacent to the blood vessel, where the catheters include a catheter shaft. The catheters also include one or more light guides disposed along the catheter shaft and within a balloon. Each light guide can be configured to be in optical communication with a light and/or power source.

Those of ordinary skill in the art will realize that the following detailed description of the present invention is illustrative only and is not intended to be in any way limiting. Other embodiments of the present invention will readily suggest themselves to such skilled persons having the benefit of this disclosure. Additionally, other methods of delivering energy to the lesion can be utilized, including, but not limited to electric current induced plasma generation. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

As an overview, in certain embodiments, the light guides can be configured to include one or more diverting features configured to direct light to exit from the light guide toward a side surface of the light guide and toward the balloon wall. The diverting features can direct light to exit in a direction away from the axis of the light guide, or in an off-axis direction. Additionally, or in the alternative, the light guides can each include one or more light windows disposed along the longitudinal or axial surfaces of each light guide and in optical communication with a diverting feature. The light windows can include a portion of the light guide that allows light to exit the light guide from within the light guide, such as a portion of the light guide lacking a cladding material on or about the light guide. The inflatable balloons described herein can be coupled to the catheter shaft and/or other structures, and can be inflated with a balloon fluid.

The inflatable balloon can include a balloon wall and can be configured to expand from a deflated state suitable for advancing the catheter through a patient's vasculature to an inflated state suitable for anchoring the catheter in position relative to a treatment site. The power source can be configured to provide sub-millisecond pulses of a light from the power source to initiate plasma formation in a balloon fluid within the balloon to cause rapid bubble formation and to impart pressure waves upon the treatment site.

Various embodiments of this invention shine laser light energy onto a plasma target to cause plasma generation via interaction with plasma target material rather than optical breakdown of the balloon fluid thereby moving the plasma creation away from a distal end of the optical fiber (light guide). This can be accomplished by positioning the plasma target away from the distal end of the optical fiber to absorb the light energy and convert it into a plasma at some distance away from the distal end of the light guide.

As used herein, the terms "intravascular lesion" and "vascular lesion" are used interchangeably unless otherwise noted.

It is appreciated that the catheter systems herein can include many different forms. Referring now to FIG. 1, a schematic cross-sectional view is shown of a catheter system in accordance with various embodiments herein. A catheter system 100 is suitable for imparting pressure to induce fractures in a vascular lesion within or adjacent a vessel wall of a blood vessel. In the embodiment illustrated in FIG. 1, the catheter system 100 can include one or more of a catheter 102, one or more light guides 122, a power source 124, a manifold 136 and a fluid pump 138.

The catheter 102 includes an inflatable balloon 104 (sometimes referred to herein as "balloon"). The catheter 102 is configured to move to a treatment site 106 within or adjacent to a blood vessel 108. The treatment site 106 can include a vascular lesion such as a calcified vascular lesion, for example. Additionally, or in the alternative, the treatment site 106 can include a vascular lesion such as a fibrous vascular lesion.

The catheter 102 can include the balloon 104, a catheter shaft 110 and a guidewire 112. The balloon can be coupled to the catheter shaft 110. The balloon can include a balloon proximal end 104P and a balloon distal end 104D. The catheter shaft 110 can extend between a shaft proximal end 114 and a shaft distal end 116. The catheter shaft 110 can include a guidewire lumen 118 which is configured to move over the guidewire 112. The catheter shaft 110 can also include an inflation lumen (not shown). In some embodiments, the catheter 102 can have a distal end opening 120 and can accommodate and be moved over and/or along the guidewire 112 so that the balloon 104 is positioned at or near the treatment site 106.

The catheter shaft 110 of the catheter 102 can encircle one or more light guides 122 (only one light guide 122 is illustrated in FIG. 1 for clarity) in optical communication with a power source 124. The light guide 122 can be at least partially disposed along and/or within the catheter shaft 110 and at least partially within the balloon 104. In various embodiments, the light guide 122 can be an optical fiber and the power source 124 can be a laser. The power source 124 can be in optical communication with the light guide 122. In some embodiments, the catheter shaft 110 can encircle multiple light guides such as a second light guide, a third light guide, etc.

The balloon 104 can include a balloon wall 130. The balloon 104 can expand from a collapsed configuration suitable for advancing at least a portion of the catheter shaft 102 through a patient's vasculature to an expanded configuration suitable for anchoring the catheter 102 into position relative to the treatment site 106. The power source 124 of the catheter system 100 can be configured to provide sub-millisecond pulses of light from the power source 124, along the light guide 112, to a location within the balloon 104. The pulses of light, resulting in light energy, thereby induce plasma formation in a balloon fluid 132 within the balloon 104. The plasma formation causes rapid bubble formation, and imparts pressure waves upon the treatment site 106. Exemplary plasma-induced bubbles are shown as bubbles 134 in FIG. 1. The balloon fluid 132 can be a liquid or a gas. As provided in greater detail herein, the plasma-induced bubbles 134 are intentionally formed at some distance away from the light guide 122 so that the likelihood of damage to the light guide is decreased.

In various embodiments, the sub-millisecond pulses of light can be delivered to near the treatment site 106 at a frequency of from at least approximately 1 hertz (Hz) up to approximately 5000 Hz. In some embodiments, the sub-millisecond pulses of light can be delivered to near the treatment site 106 at a frequency from at least 30 Hz to 1000 Hz. In other embodiments, the sub-millisecond pulses of light can be delivered to near the treatment site 106 at a frequency from at least 10 Hz to 100 Hz. In yet other embodiments, the sub-millisecond pulses of light can be delivered to near the treatment site 106 at a frequency from at least 1 Hz to 30 Hz. In some embodiments, the sub-millisecond pulses of light can be delivered to near the treatment site 106 at a frequency that can be greater than or equal to 1 Hz, 2 Hz, 3 Hz, 4 Hz, 5 Hz, 6 Hz, 7 Hz, 8 Hz, or 9 Hz, 10 Hz, 20 Hz, 30 Hz, 40 Hz, 50 Hz, 60 Hz, 70 Hz, 80 Hz, 90 Hz, 100 Hz, 200 Hz, 300 Hz, 400 Hz, 500 Hz, 600 Hz, 700 Hz, 800 Hz, 900 Hz, 1000 Hz, 1250 Hz, 1500 Hz, 1750 Hz, 2000 Hz, 2250 Hz, 2500 Hz, 2750 Hz, 3000 Hz, 3250 Hz, 3500 Hz, 3750 Hz, 4000 Hz, 4250 Hz, 4500 Hz, 4750 Hz, or 5000 Hz or can be an amount falling within a range between any of the foregoing. Alternatively, the sub-millisecond pulses of light can be delivered to near the treatment site 106 at a frequency that can be greater than 5000 Hz.

It is appreciated that the catheter system 100 herein can include any number of light guides 122 in optical communication with the power source 124 at the proximal portion 114, and with the balloon fluid 132 within the balloon 104 at the distal portion 116. For example, in some embodiments, the catheter system 100 herein can include from one light guide 122 to five light guides 122. In other embodiments, the catheter system 100 herein can include from five light guides to fifteen light guides. In yet other embodiments, the catheter system 100 herein can include from ten light guides to thirty light guides. The catheter system 100 herein can include 1-30 light guides. It is appreciated that the catheter system 100 herein can include any number of light guides that can fall within a range, wherein any of the forgoing numbers can serve as the lower or upper bound of the range, provided that the lower bound of the range is a value less than the upper bound of the range. In some embodiments, the catheter system 100 herein can include greater than 30 light guides.

The manifold 136 can be positioned at or near the shaft proximal end 114. The manifold 136 can include one or more proximal end openings that can receive the one or more light guides, such as light guide 122, the guidewire 112, and/or an inflation conduit 140. The catheter system 100 can also include the fluid pump 138 that is configured to inflate the balloon 104 with the balloon fluid 132 and/or deflate the balloon 104 as needed.

As with all embodiments illustrated and described herein, various structures may be omitted from the figures for clarity and ease of understanding. Further, the figures may include certain structures that can be omitted without deviating from the intent and scope of the invention.

Figure 2:
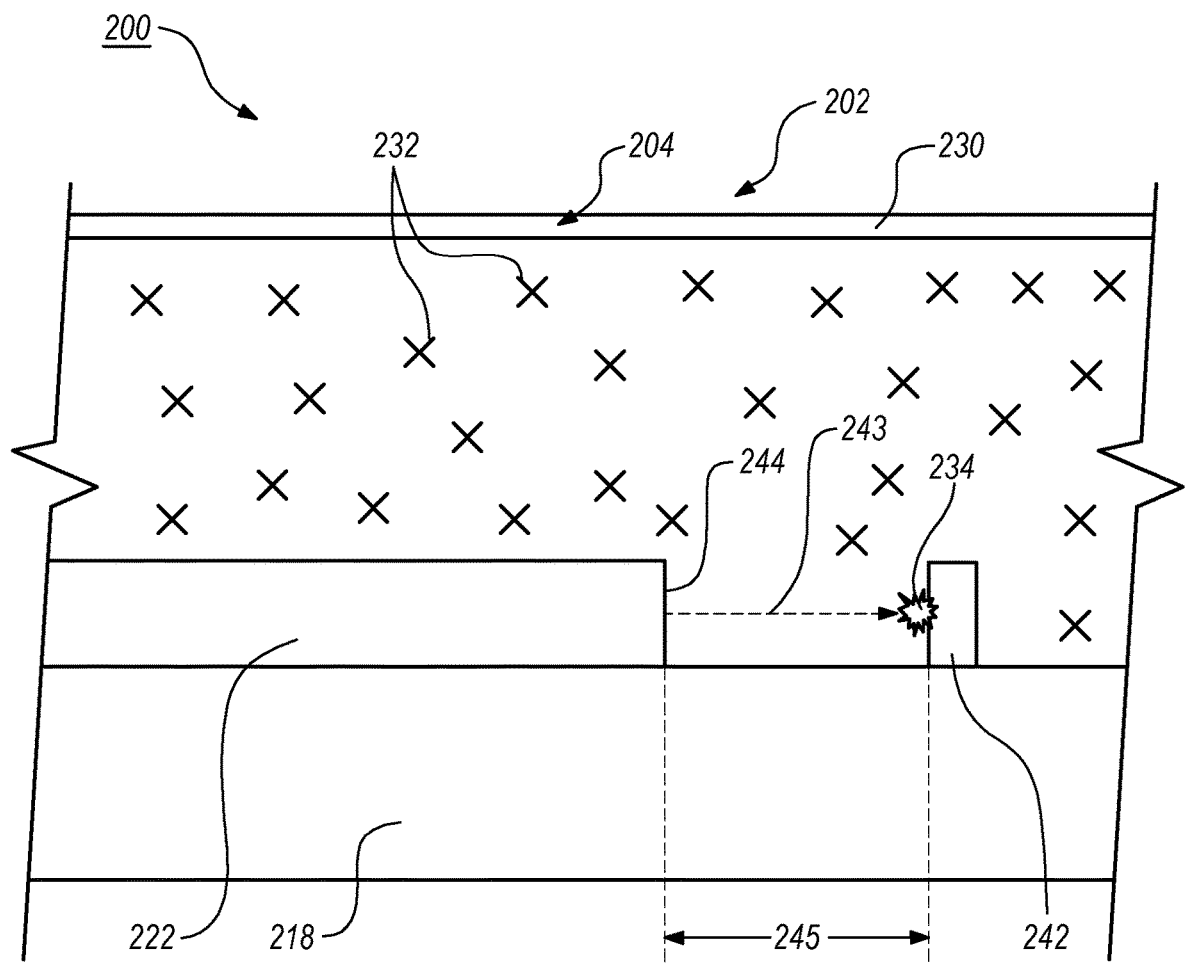
FIG. 2 is a simplified schematic side view of one embodiment of a portion of the catheter system, including one embodiment of a portion of a catheter.

FIG. 2 is a simplified schematic side view of one embodiment of a portion of the catheter system 200, including one embodiment of a portion of a catheter 202. In the embodiment illustrated in FIG. 2, the catheter system can include one or more of an inflatable balloon 204, a guidewire lumen 218 and a light guide 222. Although the light guide 222 in FIG. 2 (as well as other embodiments shown and/or described herein) is illustrated as being positioned adjacent to the guidewire lumen 218, it is understood that in some embodiments, the light guide 222 can be positioned within the guidewire lumen 218 or the catheter shaft 110 (illustrated in FIG. 1), or the light guide 222 can be incorporated into a portion of the guidewire lumen 218 or the catheter shaft 110. In still other embodiments, the light guide 222 can be positioned away from the guidewire lumen 218 and/or the catheter shaft 110. In yet other embodiments, the guidewire lumen 218 can be omitted from the catheter system 200. It is further recognized that the structures included in FIG. 2 (as well as other figures shown and described herein) are not necessarily drawn to scale for ease of viewing and/or understanding.

In the embodiment illustrated in FIG. 2, the catheter system 200 also includes a plasma target 242 that is spaced apart from the distal tip 244 of the light guide 222. The plasma target 242 can be formed from various materials. In some embodiments, the plasma target 242 can be formed from metallics and/or metal alloys having relatively high melting temperatures, such as tungsten, tantalum, molybdenum, niobium, platinum and/or iridium. Alternatively, the plasma target 242 can be formed from at least one of magnesium oxide, beryllium oxide, tungsten carbide, titanium nitride, titanium carbonitride and titanium carbide. Still alternatively, the plasma target 242 can be formed from at least one of diamond CVD and diamond. In other embodiments, the plasma target 242 can be formed from transition metal, an alloy metal or a ceramic material. Still alternatively, the plasma target 242 can be formed from any other suitable material(s). As provided in greater detail herein, the geometry, configuration, size and/or shape of the plasma target 242 can also be varied to suit the design requirements of the catheter system 200.

In the embodiment illustrated in FIG. 2, the light guide 222 emits light energy 243 (illustrated in dashed lines in FIG. 2) from a distal tip 244 of the light guide 222 toward the plasma target 242. The plasma target 242 is spaced apart from the distal tip 244 of the light guide by a target gap distance 245. The target gap distance 245 can vary. For example, in various embodiments, the target gap distance 245 can be at least 1 µm, at least 10 µm, at least 100 µm, at least 1 mm, at least 2 mm, at least 3 mm, at least 5 mm or at least 1 cm. The target gap distance 245 can vary depending upon the size, shape and/or angle of the plasma target 242 relative to the light energy emitted by the light guide 222, the type of material used to form the plasma target 242, the quantity and/or duration of the light energy being emitted from the light guide 222, the type of balloon fluid 232 used in the balloon 204, etc.

In certain embodiments, the plasma target 242 can be secured to another structure of the catheter system 200. For example, the plasma target 242 can be fixedly or movably secured or coupled to the guidewire lumen 218, as illustrated in FIG. 2. Alternatively, the plasma target 242 can be fixedly or movably secured or coupled to the light guide 222 or another suitable structure. Still alternatively, the plasma target 242 can be suspended (unsecured) within the balloon fluid 232.

With this design, the light energy 243 generates a plasma bubble 234, which creates an outwardly emanating pressure wave (not shown) throughout the balloon fluid 232 that impacts the balloon 204. The impact to the balloon 204 causes the balloon to forcefully disrupt and/or fracture the vascular lesion, e.g. a calcified vascular lesion, at the treatment site 106 (illustrated in FIG. 1). In other words, the associated rapid formation of the plasma bubble 234 and resulting localized balloon fluid 232 velocity within the balloon 204 transfers mechanical energy though the incompressible balloon fluid 232 to impart a fracture force on the treatment site 106. The rapid change in momentum of the balloon fluid 232 upon hitting the balloon wall 230 is known as hydraulic shock, or water hammer. The change in momentum of the balloon fluid 232 is transferred as a fracture force to the vascular lesion which is opposed to the balloon wall 230.

By positioning the plasma target 242 away from the distal tip 244 of the light guide 222, damage to the light guide 222 from the plasma bubble 234 is less likely to occur than if the plasma bubble 234 was generated at or more proximate the distal tip 244 of the light guide. Stated another way, the presence of the plasma target 242, and positioning the plasma target 242 away from the distal tip 244 of the light guide 222, causes the plasma bubble 234 to in turn be generated away from the distal tip 244 of the light guide 222, reducing the likelihood of damage to the light guide 222.

Further, in this embodiment, the positioning of the plasma target 242 can also be different from those previously described.

Figure 3A:
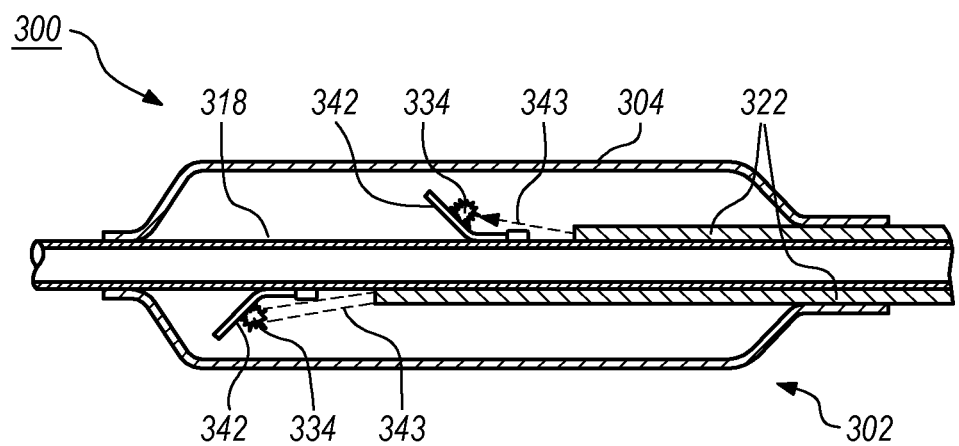
FIG. 3A is a simplified schematic side view of one embodiment of a portion of the catheter system, including another embodiment of a portion of the catheter, shown in an inflated state.

FIG. 3A is a simplified schematic side view of another embodiment of a portion of the catheter system 300, including another embodiment of a portion of the catheter 302, shown in an inflated state. In this embodiment, the catheter 302 includes a balloon 304, a guidewire lumen 318, one or more light guides 322 (two light guides 322 are illustrated in FIG. 3A) and one or more plasma targets 342 (two plasma targets 342 are illustrated in FIG. 3A). In the embodiment illustrated in FIG. 3A, the light guides 322 can be substantially similar to the light guides previously shown and described herein and/or shown in greater detail below.

However, in this embodiment, the plasma targets 342 can be movable depending upon the inflation status of the balloon 304. For example, the plasma targets 342 can include springs, e.g. can be spring-loaded, that extend outwardly toward the balloon 304 when the balloon 304 is in the inflated state. Stated another way, the plasma targets 342 can move and/or extend toward the balloon 304 (or in another suitable direction) so that the light energy 343 from the light guide(s) 322 is better directed toward the plasma target(s) 342. As previously described herein, because the plasma target 342 is positioned away from the distal tip 344 of the light guide 322, the plasma bubble 334 that is generated is less likely to cause damage to the light guide than if the plasma bubble 334 were generated at or more near to the light guide 322.

Further, in this embodiment, the positioning of the plasma targets 342 can be staggered (with two or more plasma targets 342) so that a greater area of the balloon 304 can be impacted by the resultant pressure wave(s) from the plasma bubbles 334.

Figure 3B:
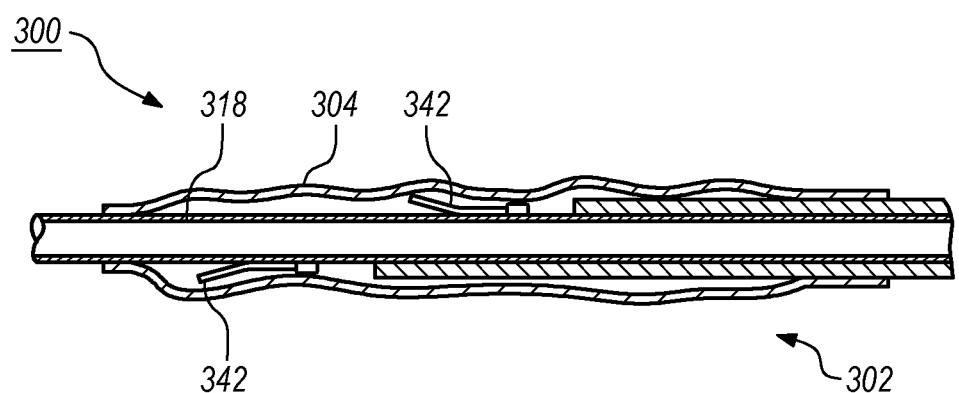
FIG. 3B is a simplified schematic side view of the portion of the catheter illustrated in FIG. 3A, shown in a deflated state.

FIG. 3B is a simplified schematic side view of the portion of the catheter illustrated in FIG. 3A, shown in a deflated state. In this embodiment, upon deflation of the balloon 304, the plasma targets 342 can retract or otherwise move back toward the guidewire lumen 318, or in another suitable direction, so that the catheter 302 can have a somewhat smaller diameter during insertion and/or removal of the catheter 302 from the blood vessel 108 (illustrated in FIG. 1), thereby increasing the ease of insertion and/or removal by the operator of the catheter system 300.

Figure 4:
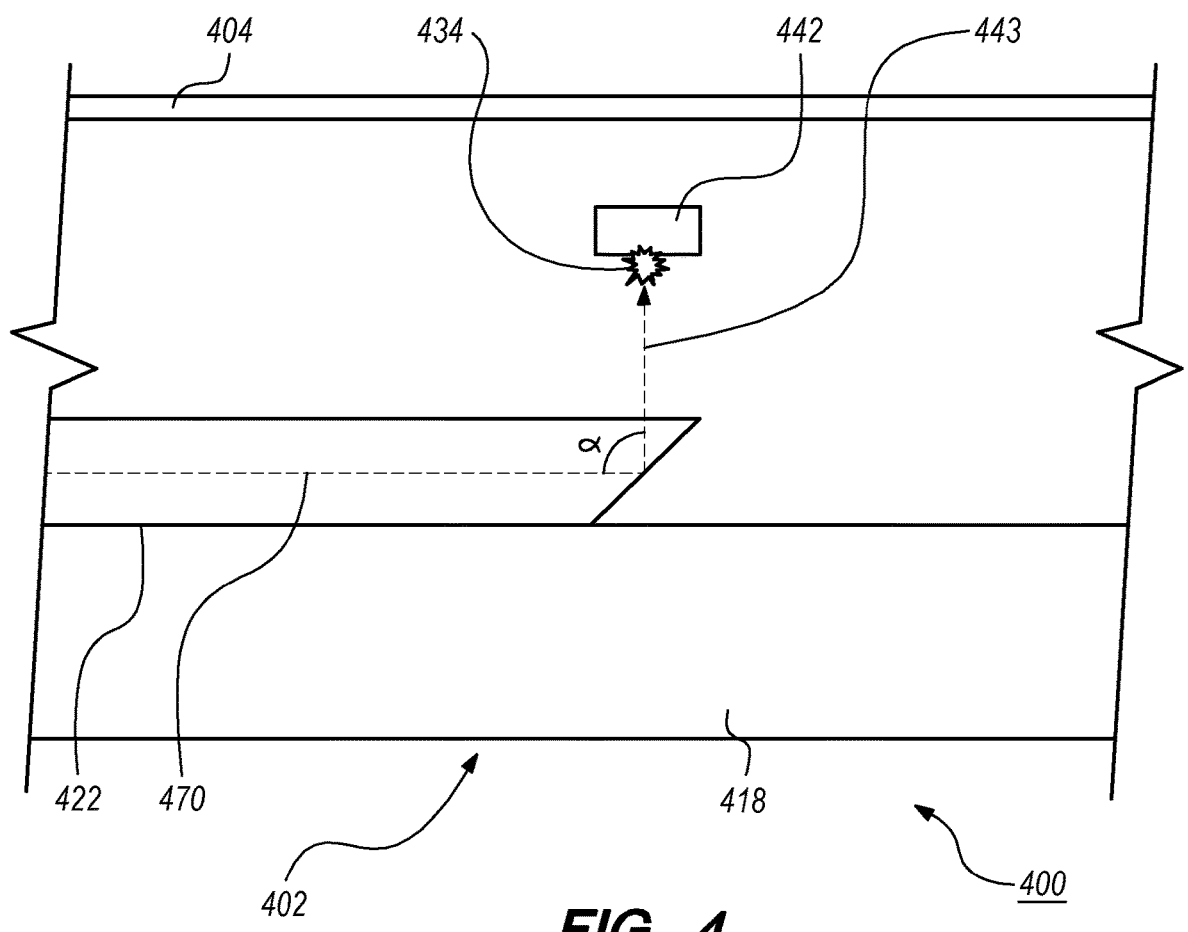
FIG. 4 is a simplified schematic side view of one embodiment of a portion of the catheter system, including another embodiment of a portion of the catheter.

FIG. 4 is a simplified schematic side view of another embodiment of a portion of the catheter system 400, including another embodiment of a portion of the catheter 402. In the embodiment illustrated in FIG. 4, the catheter 402 includes a balloon 404, a guidewire lumen 418, one or more light guides 422 and one or more plasma targets 442.

The operation and function of the light guide 422 and the plasma target 442 can be substantially similar to those previously described. However, in this embodiment, the light guide 422 can be configured to redirect the light energy 443 in a different direction, i.e. non-parallel with a longitudinal axis 470 of the light guide 422. For example, the light energy can be redirected at an angle α relative to the longitudinal axis 470 of the light guide 422. In the embodiment illustrated in FIG. 4, the light energy 443 is redirected in a direction that is somewhat perpendicular to the longitudinal axis 470 of the light guide 422. However, it is understood that this type of angle is provided for ease of understanding only, and that any angle α between 0 and 180 degrees relative to the longitudinal axis 470 of the light guide 422 can be used. The structures and methods for redirecting the light energy 443 in this manner are provided in greater detail herein.

Further, in this embodiment, the positioning of the plasma target 442 can also be different from those previously described. For example, in one embodiment, the plasma target 442 is positioned between the light guide 422 and the balloon 404. In various embodiments, the plasma target 442 can be secured or coupled to another structure within the catheter 402, such as the guidewire lumen 418, the light guide 422, the balloon 404, or any other suitable structure. With this design, the plasma bubble 434 can be generated more proximate to the balloon 404, which can be beneficial for exerting a greater force to disrupt and/or fracture the calcified lesion and/or to maintain a spacing between the formation of the plasma bubble 434 and the light guide 422 for reasons provided herein.

Figure 5:
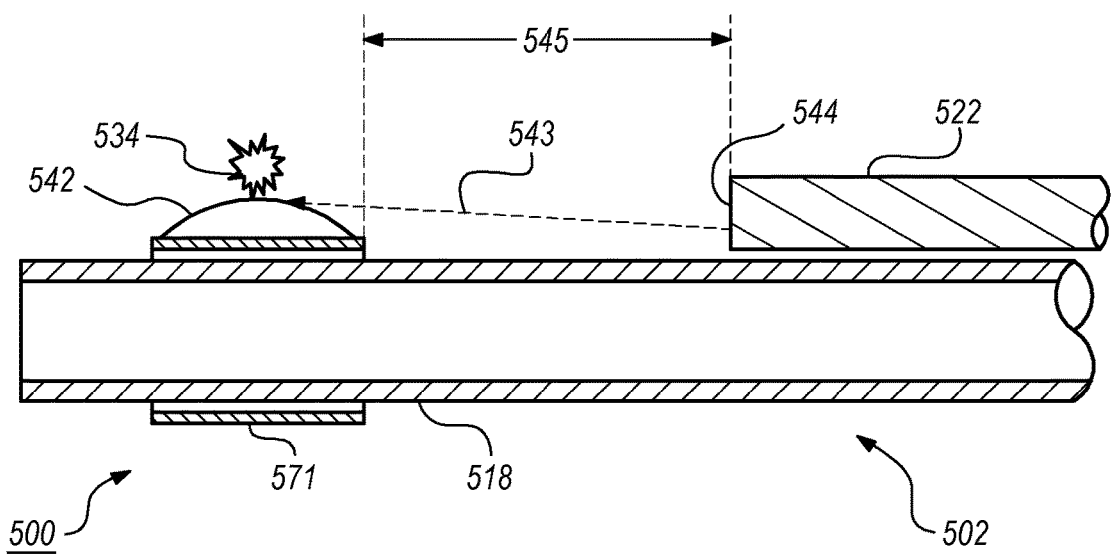
FIG. 5 is a simplified schematic side view of one embodiment of a portion of the catheter system, including another embodiment of a portion of the catheter.

FIG. 5 is a simplified cross-sectional view of another embodiment of a portion of the catheter system 500, including another embodiment of a portion of the catheter 502. In the embodiment illustrated in FIG. 5, the balloon has been omitted for clarity. In this embodiment, the catheter 502 includes a guidewire lumen 518, one or more light guides 522, one or more plasma targets 542 and a target coupler 571.

The operation and function of the light guide 522 and the plasma target 542 can be substantially similar to those previously described. However, in this embodiment, the plasma target 542 is coupled to the guidewire lumen 518 (or another suitable structure) with the target coupler 571. In one embodiment, the target coupler 571 can be a ring-like structure that secures the plasma target 542 to the guidewire lumen 518 (or another structure). The light energy 543 is emitted from the light guide 522, and results in a plasma bubble 534 being generated at the plasma target 542. Alternatively, the plasma target 542 can be adhered directly to the guidewire lumen 518 (or another structure) with adhesive or any other means for securing the plasma target 542. Still alternatively, the target coupler 571 can be movable so that the plasma target 542 can be moved either manually or automatically along the guidewire lumen 518 to change the target gap distance 545 between the plasma target 542 and the distal tip 544 of the light guide 522.

Additionally, or in the alternative, the shape of the plasma target 542 can vary. For example, in the embodiment illustrated in FIG. 5, the plasma target 542 can have a somewhat dome-shape or convex configuration. Still alternatively, the plasma target 542 can have another suitable configuration. With these designs, the plasma bubble 534 can be generated at the plasma target 542, and the plasma target 542 can redirect the resultant pressure wave in any desired direction to achieve the desired results.

Figure 6:
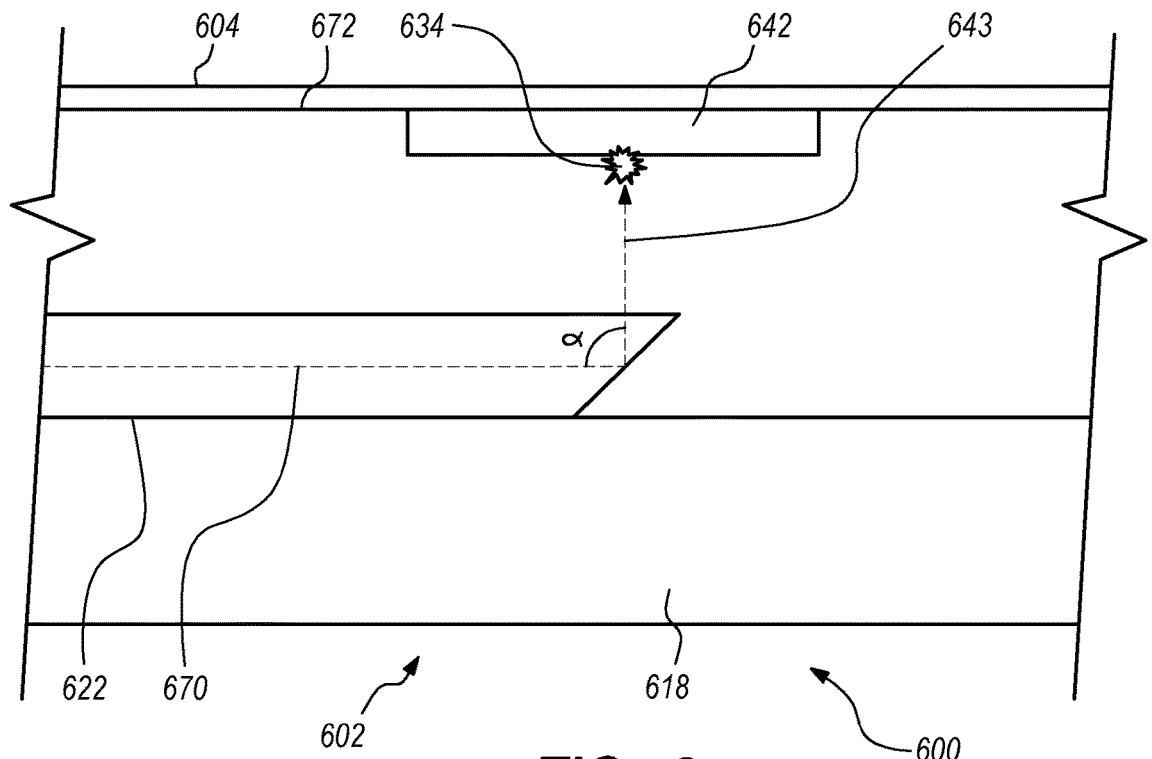
FIG. 6 is a simplified schematic side view of one embodiment of a portion of the catheter system, including another embodiment of a portion of the catheter.

FIG. 6 is a simplified schematic side view of another embodiment of a portion of the catheter system 600, including another embodiment of a portion of the catheter 602. In the embodiment illustrated in FIG. 6, the catheter 602 includes a balloon 604, a guidewire lumen 618, one or more light guides 622 and one or more plasma targets 642.

The operation and function of the light guide 622 and the plasma target 642 can be substantially similar to those previously described. However, in this embodiment, the plasma target 642 is secured to a balloon inner surface 672 of the balloon 604. With this design, the plasma bubble is generated away from the light guide 622, thereby decreasing the likelihood of damage to the light guide 622. Moreover, because the plasma target 642 is positioned on the balloon inner surface 672, the balloon will receive a near-direct force from the plasma bubble 634 to increase the disruptive force upon the calcified lesion.

In this embodiment, the light guide 622 can be configured to redirect the light energy 643 in a different direction, i.e. non-parallel with a longitudinal axis 670 of the light guide 622. For example, the light energy can be redirected at an angle α relative to the longitudinal axis 670 of the light guide 622. In the embodiment illustrated in FIG. 6, the light energy 643 is redirected in a direction that is somewhat perpendicular to the longitudinal axis 670 of the light guide 622. However, it is understood that this type of angle is provided for ease of understanding only, and that any angle α between 0 and 180 degrees relative to the longitudinal axis 670 of the light guide 622 can be used. The structures and methods for redirecting the light energy 643 in this manner are provided in greater detail herein.

Further, in this embodiment, the positioning of the plasma target 642 can also be different from those previously described. For example, in one embodiment, the plasma target 642 is positioned between the light guide 622 and the balloon 604. In various embodiments, the plasma target 642 can be secured or coupled to another structure within the catheter 602, such as the guidewire lumen 618, the light guide 622, the balloon 604, or any other suitable structure. With this design, the plasma bubble 634 can be generated more proximate to the balloon 604, which can be beneficial for exerting a greater force to disrupt and/or fracture the calcified lesion and/or to maintain a spacing between the formation of the plasma bubble 634 and the light guide 622 for reasons provided herein.

Figure 7A:
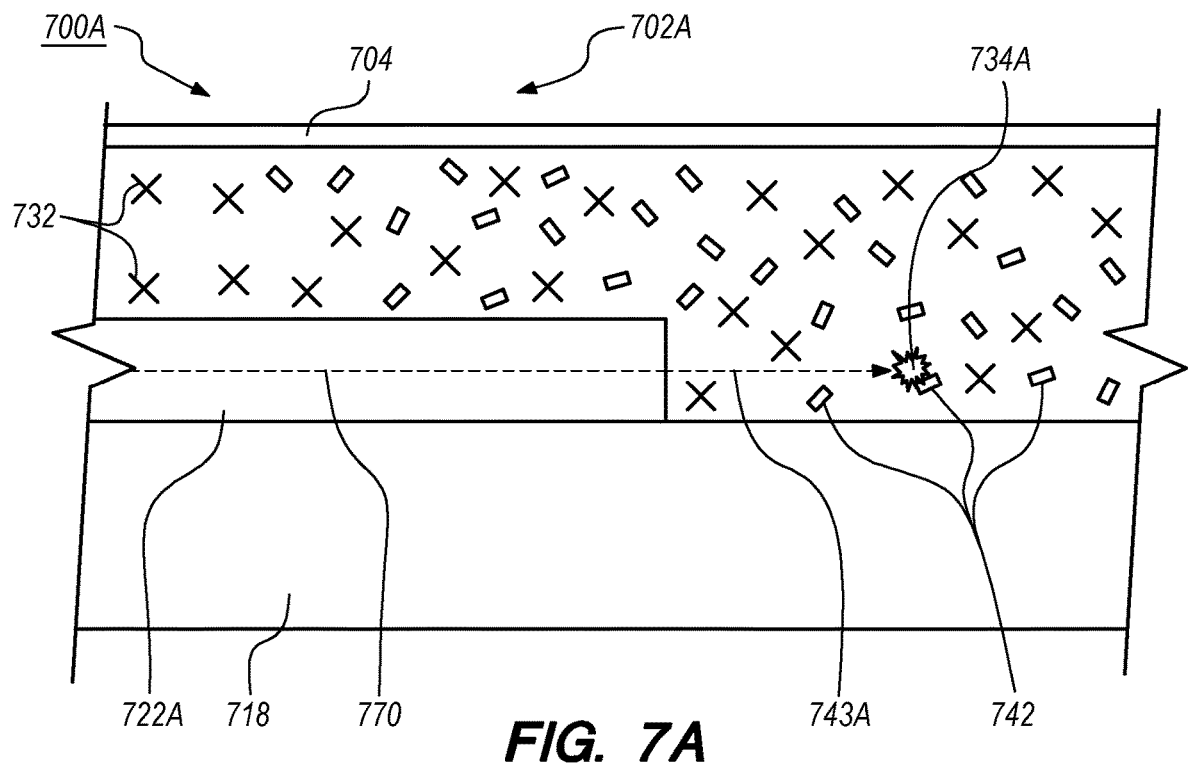
FIG. 7A is a simplified schematic side view of one embodiment of a portion of the catheter system, including another embodiment of a portion of the catheter.

FIG. 7A is a simplified schematic side view of another embodiment of a portion of the catheter system 700A, including another embodiment of a portion of the catheter 702A. In the embodiment illustrated in FIG. 7A, the catheter 702A includes a balloon 704, a guidewire lumen 718, one or more light guides 722A and a plurality of plasma targets 742.

The operation and function of the light guide 722A and the plasma targets 742 can be substantially similar to those previously described. However, in this embodiment, the light guide 722A can be configured to direct the light energy 743A parallel with a longitudinal axis 770 of the light guide 722B to generate plasma bubbles 734A at a plurality of plasma targets 742. In this embodiment, the plasma targets 742 are distributed throughout the balloon fluid 732 (illustrated as "X"'s in FIG. 7A). In this embodiment, the plasma targets 742 can be relatively small so that they can be suspended in the balloon fluid 732 more readily. In various embodiments, the plasma targets 742 can be free-floating within the balloon fluid 732, either as a homogeneous solution or a heterogeneous solution. With this design, one or more plasma bubbles 734A (only one plasma bubble 734A is illustrated in FIG. 7A) can be generated, which can be beneficial for exerting a greater force to disrupt and/or fracture the calcified lesion and/or to maintain a spacing between the formation of the plasma bubble 734A and the light guide 722A for reasons provided herein.

Figure 7B:
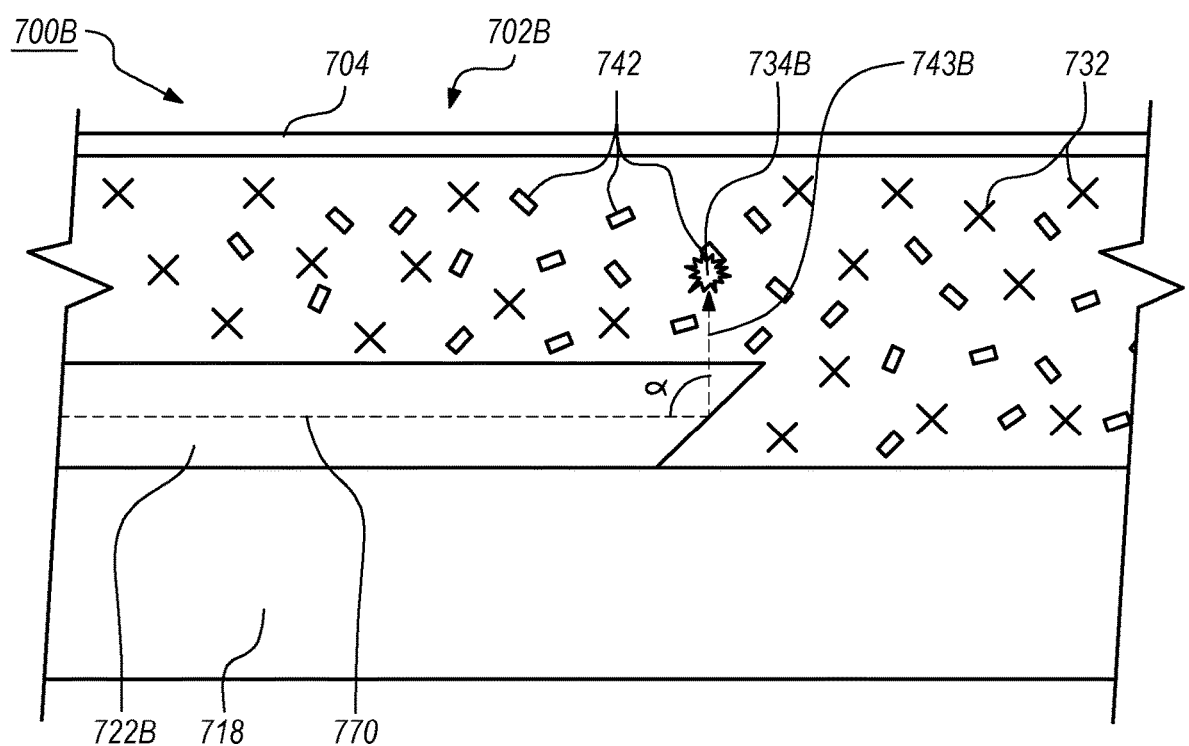
FIG. 7B is a simplified schematic side view of one embodiment of a portion of the catheter system, including another embodiment of a portion of the catheter.

FIG. 7B is a simplified schematic side view of another embodiment of a portion of the catheter system 700B, including another embodiment of a portion of the catheter 702B. In the embodiment illustrated in FIG. 7B, the catheter 702B includes a balloon 704, a guidewire lumen 718, one or more light guides 722B and a plurality of plasma targets 742.

The operation and function of the light guide 722B and the plasma targets 742 can be substantially similar to those previously described. However, in this embodiment, the light guide 722B can be configured to redirect the light energy 743B in a different direction, i.e. non-parallel with a longitudinal axis 770 of the light guide 722B. For example, the light energy 743B can be redirected at an angle α relative to the longitudinal axis 770 of the light guide 722B. In the embodiment illustrated in FIG. 7B, the light energy 743B is redirected in a direction that is somewhat perpendicular or orthogonal to the longitudinal axis 770 of the light guide 722B. However, it is understood that this type of angle is provided for ease of understanding only, and that any angle α between 0 and 180 degrees relative to the longitudinal axis 770 of the light guide 722B can be used. The structures and methods for redirecting the light energy 743B in this manner are provided in greater detail herein.

Further, in this embodiment, the positioning of the plasma targets 742 can also be different from those previously described. For example, in one embodiment, the plasma targets 742 are distributed throughout the balloon fluid 732 (illustrated as "X"'s in FIG. 7B). In this embodiment, the plasma targets 742 can be relatively small so that they can be suspended in the balloon fluid 732 more readily. In various embodiments, the plasma targets 742 can be free-floating within the balloon fluid 732, either as a homogeneous solution or a heterogeneous solution. With this design, one or more plasma bubbles 734B (only one plasma bubble 734B is illustrated in FIG. 7B) can be generated more proximate to the balloon 704, which can be beneficial for exerting a greater force to disrupt and/or fracture the calcified lesion and/or to maintain a spacing between the formation of the plasma bubble 734B and the light guide 722B for reasons provided herein.

Examples of the catheters in accordance with the various embodiments herein include those having multiple light guides disposed about the catheter shaft at different positions around the circumference, as shown in FIGS. 8-11. It is understood that multiple light guides can be used with any of the embodiments shown and/or described herein without deviating from the intent and/or scope of the invention.

Figure 8:
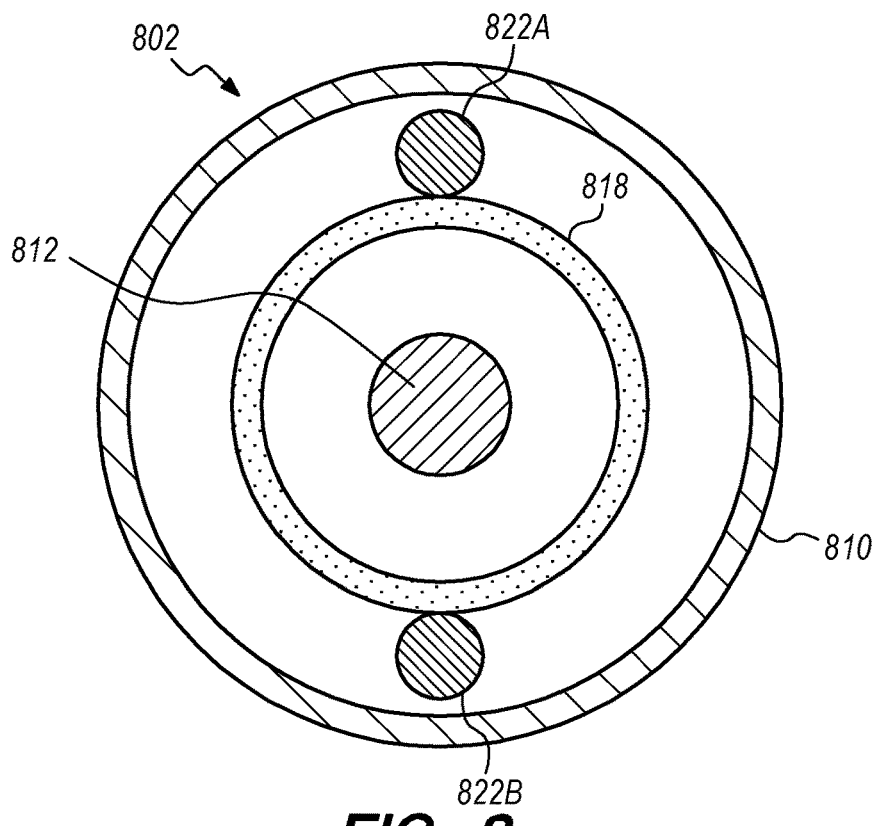
FIG. 8 is a schematic cross-sectional view of the catheter system taken on line 8-8 in FIG. 1.

Referring now to FIG. 8, a schematic cross-sectional view of a catheter 102 in FIG. 1 along line 8-8 in FIG. 1 is shown in accordance with various embodiments herein. The catheter 802 illustrated in FIG. 8 can include one or more of a catheter shaft 810, a guidewire 812, a guidewire lumen 818, a first light guide 822A and a second light guide 822B separated by about 180 degrees around the circumference from the first light guide 822A. The first light guide 822A includes a side surface that can include any surface portion about a circumference of the first light guide 822A. The second light guide 822B includes a side surface that can include any surface portion about the circumference of the second light guide 822B. In some embodiments, the side surface spans a portion of the circumference of the light guides herein, such that it is less than cylindrical. In other embodiments, the side surface can span the entire circumference of the light guides herein such that it is cylindrical. It is recognized that any light guide described herein can include a side surface about the circumference of the light guide.

Figure 9:
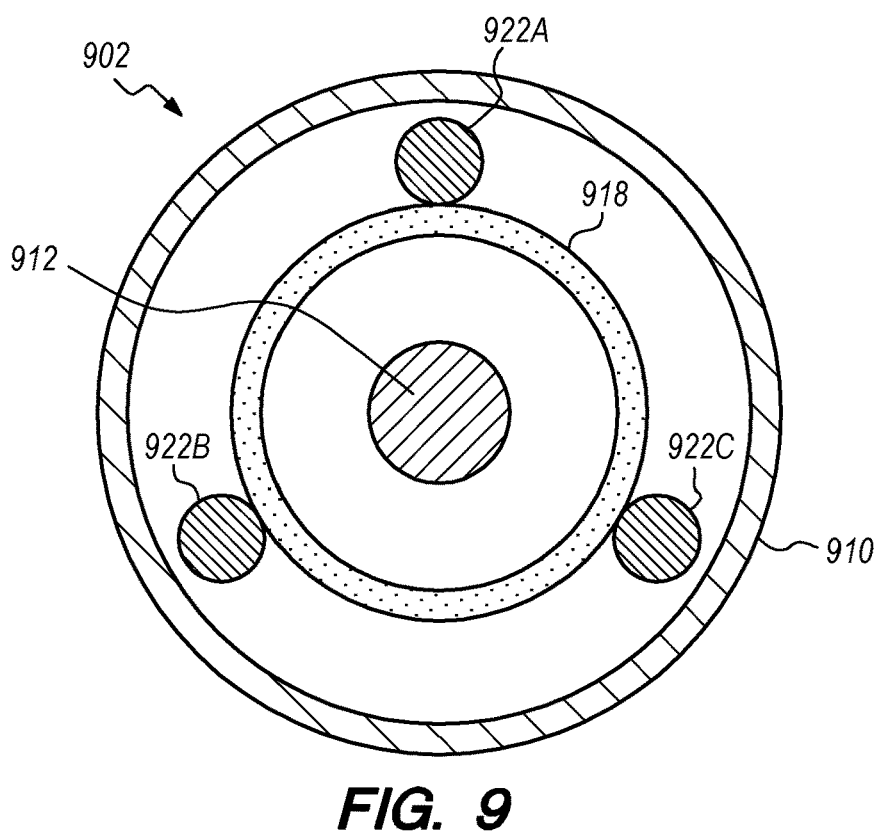
FIG. 9 is a schematic cross-sectional view of another embodiment of the catheter system.
Figure 10:
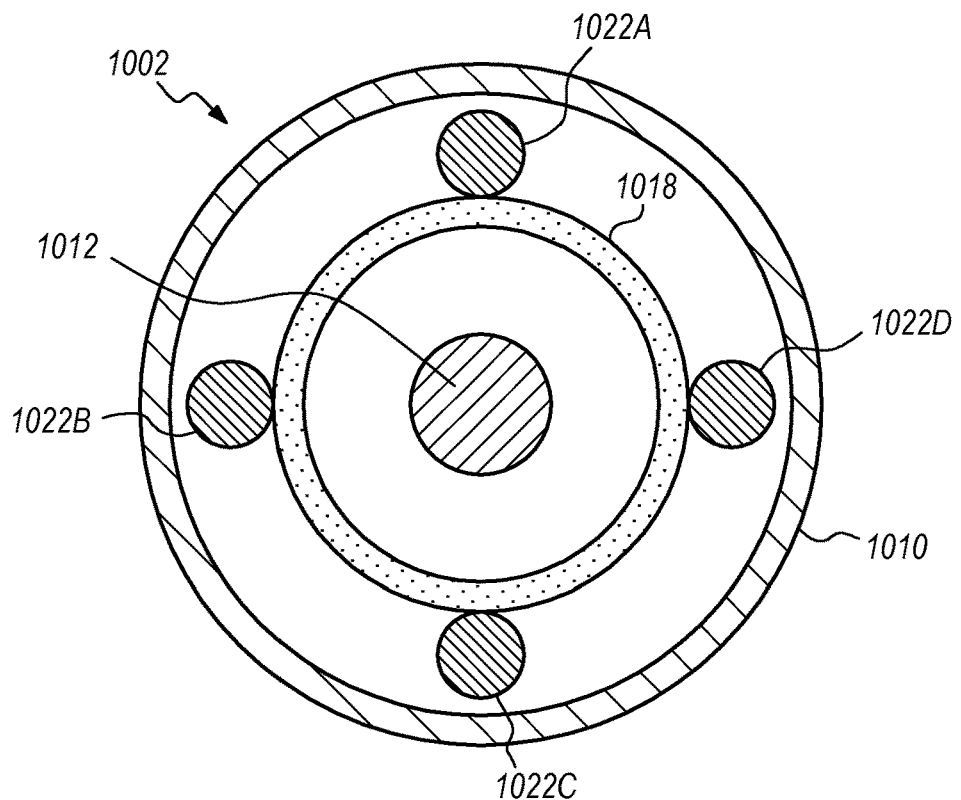
FIG. 10 is a schematic cross-sectional view of yet another embodiment of the catheter system.
Figure 11:
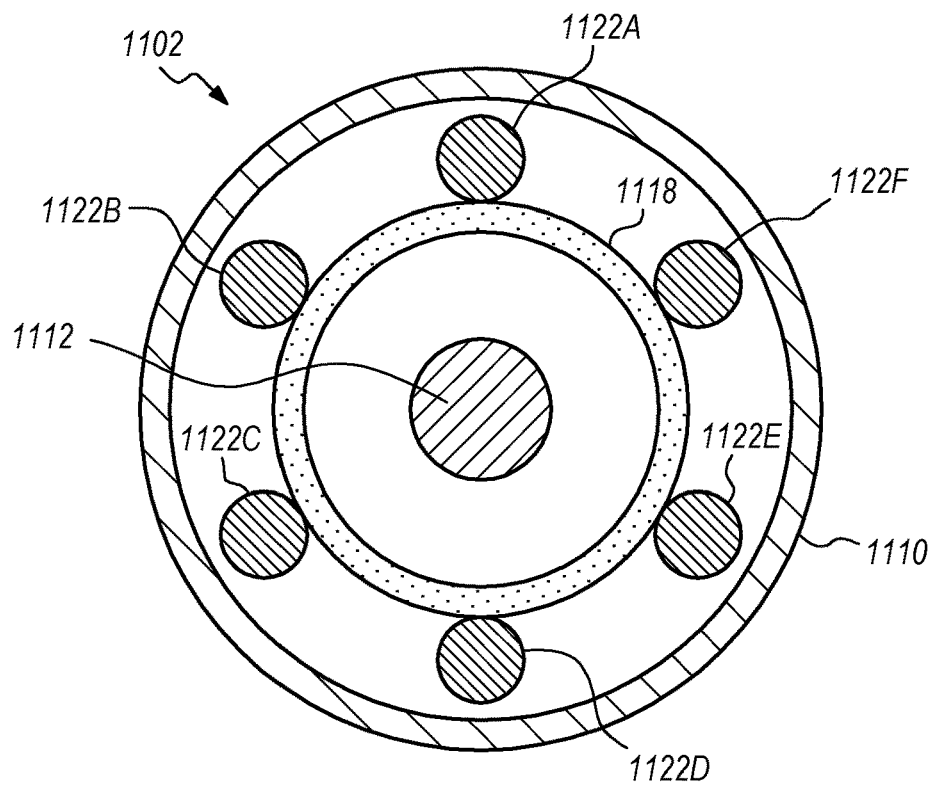
FIG. 11 is a schematic cross-sectional view of still another embodiment of the catheter system.

Referring now to FIGS. 9-11, schematic cross-sectional views of additional configurations for catheters having multiple light guides are shown in accordance with various embodiments herein. The embodiment of the catheter 902 illustrated in FIG. 3 can include one or more of a catheter shaft 910, a guidewire 912, a guidewire lumen 918, a first light guide 922A, a second light guide 922B, and a third light guide 922C separated by about 120 degrees around the circumference.

The embodiment of the catheter 1002 illustrated in FIG. 10 includes one or more of a catheter shaft 1010, a guidewire 1012, a guidewire lumen 1018, a first light guide 1022A, a second light guide 1022B, a third light guide 1022C, and a fourth light guide 1022D separated by about 90 degrees around the circumference.

The embodiment of the catheter 1102 illustrated in FIG. 11 includes one or more of a catheter shaft 1110, a guidewire 1112, a guidewire lumen 1118, a first light guide 1122A, a second light guide 1122B, a third light guide 1122C, a fourth light guide 1122D, a fifth light guide 1122E, and a sixth light guide 1122F separated by about 60 degrees around the circumference. It is understood that greater than six light guides can be used in the embodiments herein.

It is further appreciated that the light guides described herein can be disposed uniformly or nonuniformly about the catheter shaft to achieve the desired effect in the desired locations.

Diverting features and focusing features (also sometimes referred to herein simply as "diverting features") will be discussed in more detail below and in reference to FIGS. 12-15. The light guides herein can include one or more diverting features, where each diverting feature can be in optical communication with the light guide within which it is disposed. In some embodiments, the diverting features can be in optical communication with a distal end of the light guide. Referring now to FIGS. 12-15, schematic cross-sectional views of the distal ends of various shaped light guides are shown in accordance with various embodiments herein.

Figure 12:
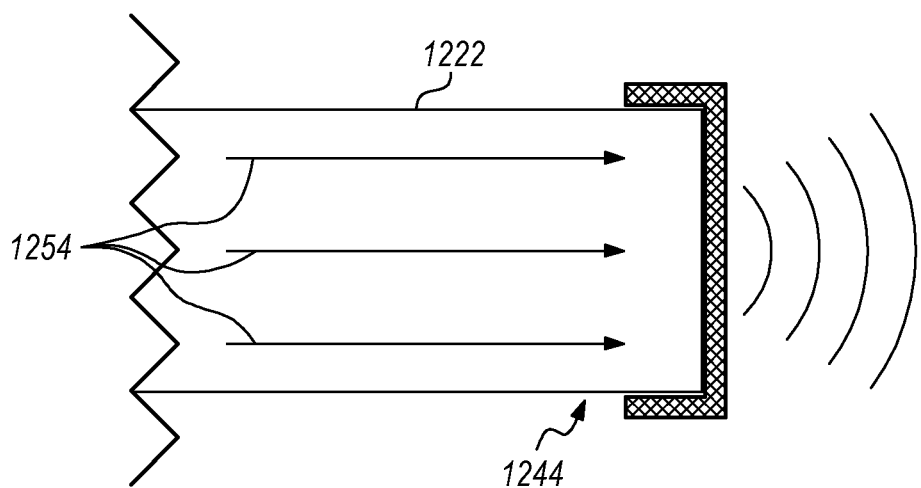
FIG. 12 is a schematic cross-sectional view of a portion of the catheter system including one embodiment of a distal portion of a light guide.
Figure 13:
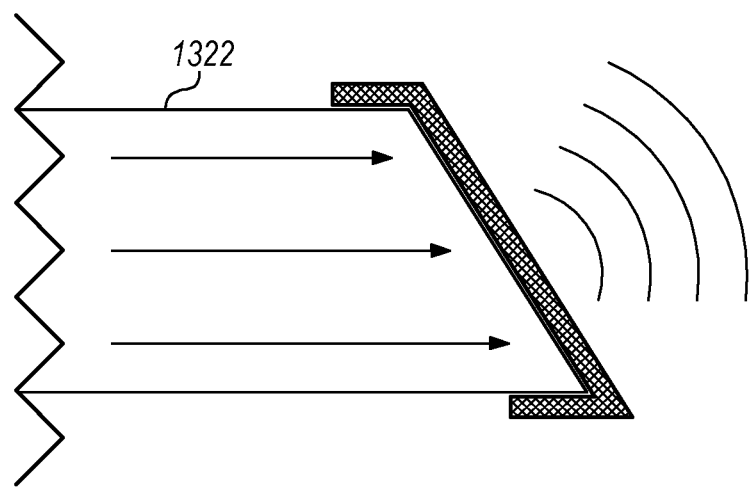
FIG. 13 is a schematic cross-sectional view of a portion of the catheter system including an embodiment of the distal portion of the light guide.
Figure 14:
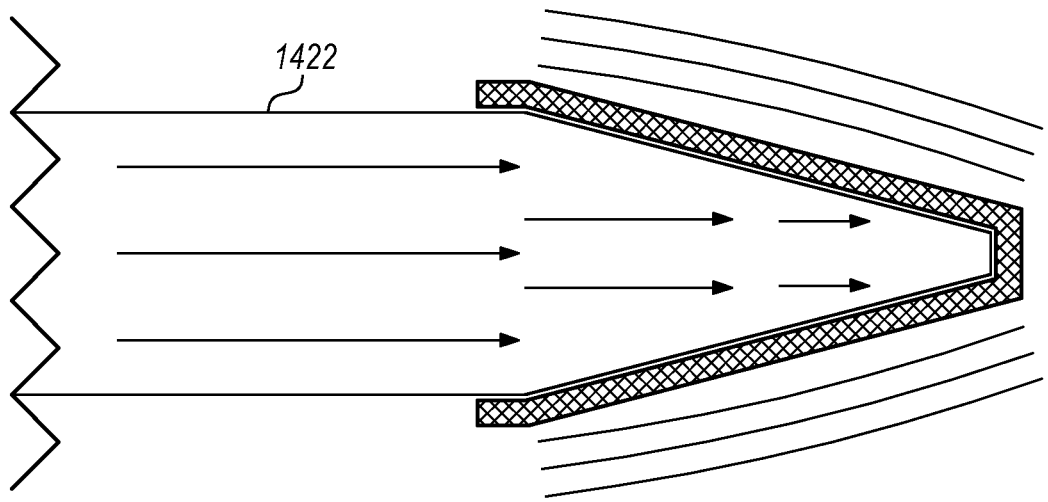
FIG. 14 is a schematic cross-sectional view of a portion of the catheter system including another embodiment of the distal portion of the light guide.

In FIG. 12, a schematic cross-sectional view of a light guide 1222 is shown. Light guide 1222 is configured such that light 1254 travels from the power source 124 (illustrated in FIG. 1) in a direction from the shaft proximal end 114 (illustrated in FIG. 1) to the distal tip 1244, as indicated by arrows 1254.

In some embodiments, the end of the light guide can have an angled shape. By way of example, in FIG. 13 a schematic cross-sectional view of a light guide 1322 is shown.

In some embodiments, the end of the light guide can have a tapered shape. By way of example, in FIG. 14 a schematic cross-sectional view of a light guide 1422 is shown.

Figure 15:
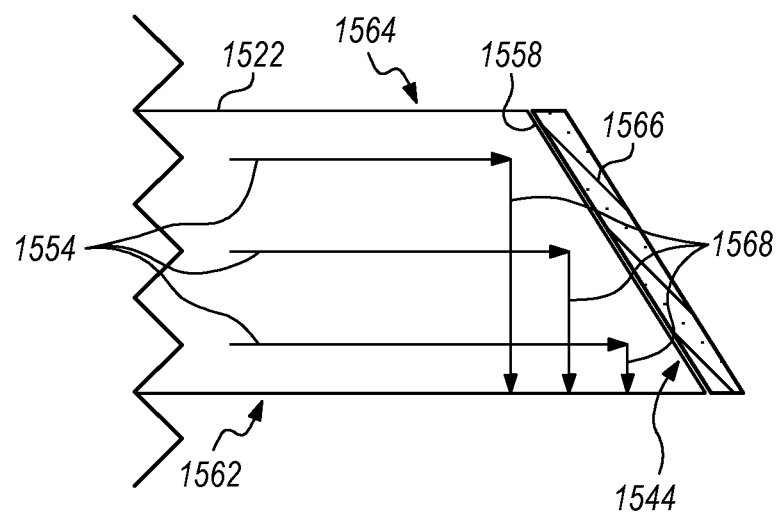
FIG. 15 is a schematic cross-sectional view of a portion of the catheter system including yet another embodiment of the distal portion of the light guide.

Referring now to FIG. 15, a schematic cross-sectional view of a light guide 1522 is shown. Light guide 1522 includes an angled end 1558 disposed on a side surface 1562 of a distal end 1564 of the light guide 1522. The light guide 1522 includes a diverting feature 1566 at the distal tip 1544 to direct the light energy 1554 within the light guide 1522 toward the side surface 1562 of the light guide 1522. Light guide 1522 is configured such that light energy 1554 travels from the distal tip 1544 in a direction that is approximately 90 degrees (or another suitable angle) from the longitudinal axis 470 (illustrated in FIG. 4, for example) as indicated by arrows 1568. Upon contact with the diverting feature 1566, the light energy 1554 is diverted, or reflected, within the light guide 1522 to a side surface 1562 of the light guide 1522. The light energy 1554 extends away from the side surface 1562 of the light guide 1522.

The diverting feature 1566 of light guide 1522 can be made from a reflecting element or a refracting element. The diverting feature 1566 can be made from a glass, a polymer, a mirror, or a reflective metal coating. It is appreciated that the angle of internal reflection by the diverting feature 1566 can be adjusted by changing the angle of the distal tip 1544 of light guide 1522.

In some embodiments, a diverting feature can be included with the light guide to direct light toward a side surface of the distal end of the light guide. A diverting feature can include any feature of the system herein that diverts light from the light guide away from its axial path toward a side surface of the light guide. Examples include a reflector, a refracting structure, and a fiber diffuser.

In some embodiments herein, the light guides can include multiple diverting features. By way of example, each light guide herein can include a first diverting feature, a second diverting feature, a third diverting feature or a fourth diverting feature. In other embodiments, each light guide can include more than four diverting features. The diverting features can be configured to direct light to exit a light guide at a side surface thereof toward the balloon wall. In some examples, the diverting feature directs light toward the balloon surface closest to the diverting feature, so that the light does not cross the longitudinal axis of the catheter on its path to the balloon surface. It is appreciated that the diverting features can be in optical communication with corresponding light window.

The diverting features herein can be configured to direct light in the light guide toward a side surface of the distal portion, where the side surface is in optical communication with a light window. It is appreciated that the light guides herein can each include multiple diverting features and multiple light windows. Examples of the diverting features suitable for use herein include a reflecting element, a refracting element and/or a fiber diffuser.

Figure 16:
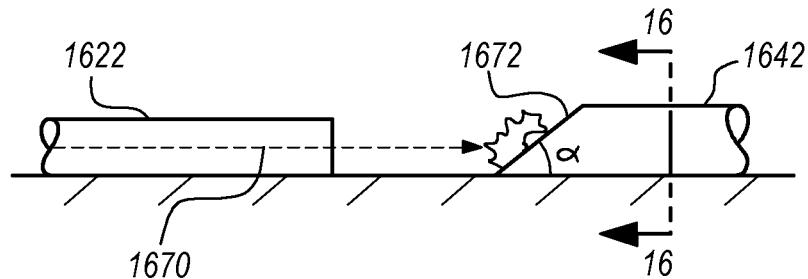
FIG. 16 is a simplified schematic side view of a portion of one embodiment of the catheter, including an embodiment of a portion of a plasma target.

FIG. 16 is a simplified schematic side view of one embodiment of a portion of a catheter, including a light guide 1622 and an embodiment of a portion of a plasma target 1642. The plasma target 1642 includes a target face 1672. The target face 1672 can have any suitable geometry, shape or configuration. In this embodiment, the light guide 1622 and the plasma target 1642 operate substantially similar to those previously shown and/or described. However, in this embodiment, the target face 1672 is angled relative to a longitudinal axis 1670 of the light guide 1622. Stated another way, the target face 1672 has an angle α that can be any angle between 0 and 180 degrees relative to the longitudinal axis 1670 of the light guide 1622.

FIGS. 16A-16J are cross-sectional views showing representative, non-exclusive, non-limiting embodiments of the cross-sectional shape of the plasma target 1642. It is understood that there are literally an infinite number of possible cross-sectional configurations for the plasma target 1642 and that it would be an impossibility to show and describe all such configurations. However, it is the intent that the scope of this invention would encompass all such potential configurations, even those that are not shown and/or described herein.

Figure 16A:
FIGS. 16A-16J are cross-sectional views of various embodiments of the plasma target taken on line 16-16 in FIG. 16.

FIG. 16A is a cross-sectional view of one embodiment of the plasma target 1642 taken on line 16-16 in FIG. 16. In this embodiment the plasma target 1642 has a substantially circular cross-sectional shape.

Figure 16B:

FIG. 16B is a cross-sectional view of another embodiment of the plasma target 1642 taken on line 16-16 in FIG. 16. In this embodiment the plasma target 1642 has a substantially vertical oval or elliptical cross-sectional shape.

Figure 16C:

FIG. 16C is a cross-sectional view of another embodiment of the plasma target 1642 taken on line 16-16 in FIG. 16. In this embodiment the plasma target 1642 has a substantially square cross-sectional shape.

Figure 16D:

FIG. 16D is a cross-sectional view of another embodiment of the plasma target 1642 taken on line 16-16 in FIG. 16. In this embodiment the plasma target 1642 has a substantially diamond, trapezoidal or parallelogram cross-sectional shape.

Figure 16E:

FIG. 16E is a cross-sectional view of another embodiment of the plasma target 1642 taken on line 16-16 in FIG. 16. In this embodiment the plasma target 1642 has a substantially hexagonal cross-sectional shape.

Figure 16F:

FIG. 16F is a cross-sectional view of another embodiment of the plasma target 1642 taken on line 16-16 in FIG. 16. In this embodiment the plasma target 1642 has a substantially horizontal oval or elliptical cross-sectional shape.

Figure 16G:

FIG. 16G is a cross-sectional view of another embodiment of the plasma target 1642 taken on line 16-16 in FIG. 16. In this embodiment the plasma target 1642 has a substantially pentagonal cross-sectional shape.

Figure 16H:
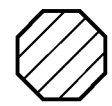

FIG. 16H is a cross-sectional view of another embodiment of the plasma target 1642 taken on line 16-16 in FIG. 16. In this embodiment the plasma target 1642 has a substantially octagonal cross-sectional shape.

Figure 16I:

FIG. 16I is a cross-sectional view of another embodiment of the plasma target 1642 taken on line 16-16 in FIG. 16. In this embodiment the plasma target 1642 has a substantially vertical rectangular cross-sectional shape.

Figure 16J:

FIG. 16J is a cross-sectional view of another embodiment of the plasma target 1642 taken on line 16-16 in FIG. 16. In this embodiment the plasma target 1642 has a substantially horizontal rectangular cross-sectional shape.

FIGS. 17A-17H are perspective views showing representative, non-exclusive, non-limiting embodiments of the geometry, shape and/or configuration of the target face 1772A-H of the plasma target 1742A-H. It is understood that there are literally an infinite number of possible cross-sectional configurations for the target face 1772A-H of the plasma target 1742A-H and that it would be an impossibility to show and describe all such configurations. However, it is the intent that the scope of this invention would encompass all such potential configurations, even those that are not shown and/or described herein.

Figure 17A:
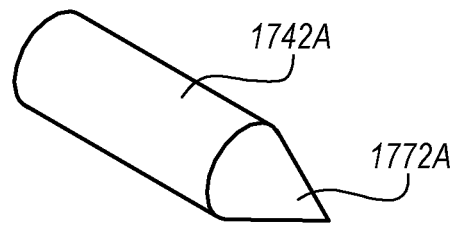
FIG. 17A-17H are perspective views of various embodiments of a portion of the plasma target having a target face.

FIG. 17A is a perspective view of a portion of an embodiment of the plasma target 1742A having one embodiment of a target face 1772A. In this embodiment, the target face 1772A has a somewhat conical configuration.

Figure 17B:
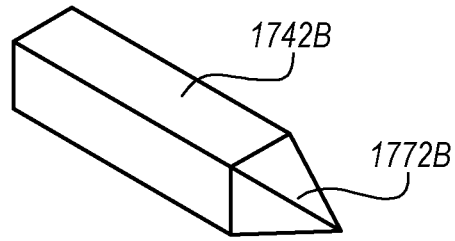

FIG. 17B is a perspective view of a portion of an embodiment of the plasma target 1742B having one embodiment of a target face 1772B. In this embodiment, the target face 1772B has a somewhat pyramidal configuration.

Figure 17C:
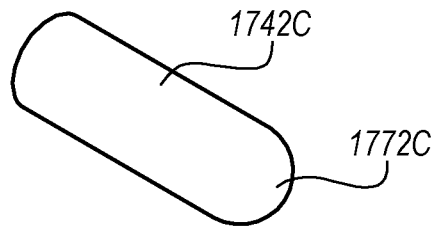

FIG. 17C is a perspective view of a portion of an embodiment of the plasma target 1742C having one embodiment of a target face 1772C. In this embodiment, the target face 1772C has a somewhat convex or dome-shaped configuration.

Figure 17D:
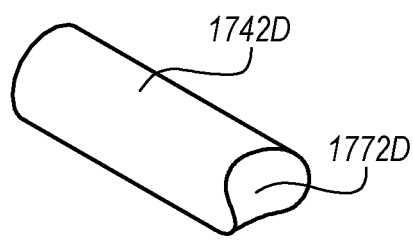

FIG. 17D is a perspective view of a portion of an embodiment of the plasma target 1742D having one embodiment of a target face 1772D. In this embodiment, the target face 1772D has a somewhat concave configuration.

Figure 17E:
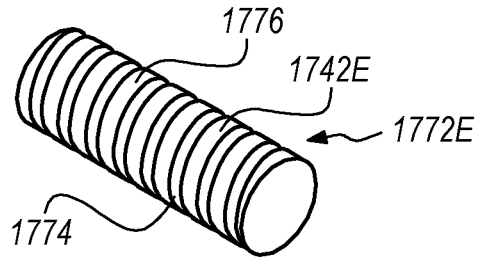

FIG. 17E is a perspective view of a portion of an embodiment of the plasma target 1742E having one embodiment of a target face 1772E. In this embodiment, the target face 1772E includes a spiral projection 1774 that extends outwardly from a side portion 1776 of the plasma target 1742E.

Figure 17F:
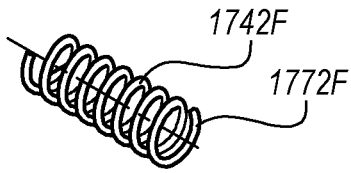

FIG. 17F is a perspective view of a portion of an embodiment of the plasma target 1742F having one embodiment of a target face 1772F. In this embodiment, the target face 1772F has a somewhat spring-like or coiled configuration.

Figure 17G:
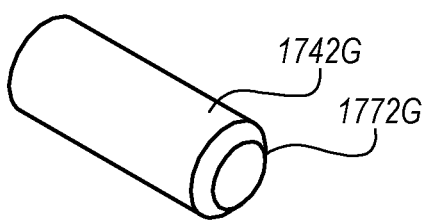

FIG. 17G is a perspective view of a portion of an embodiment of the plasma target 1742G having one embodiment of a target face 1772G. In this embodiment, the target face 1772G has a beveled configuration.

Figure 17H:
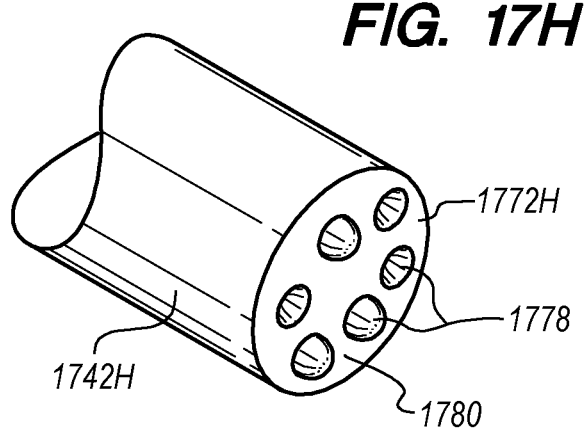

FIG. 17H is a perspective view of a portion of an embodiment of the plasma target 1742H having one embodiment of a target face 1772H. In this embodiment, the target face 1772H includes one or more surface features 1778. The surface features 1778 can include dimples, depressions or indentations that extend into a target surface 1780 of the target face 1772H. Additionally, or in the alternative, the surface features 1778 can include projections that extend outwardly from the target surface 1780 of the target face 1772H. In one embodiment, the surface features 1778 can include the same or other materials that are added to the target surface 1780. The specific sizes and/or shape(s) of the surface features 1778 can be varied.

Figure 18:
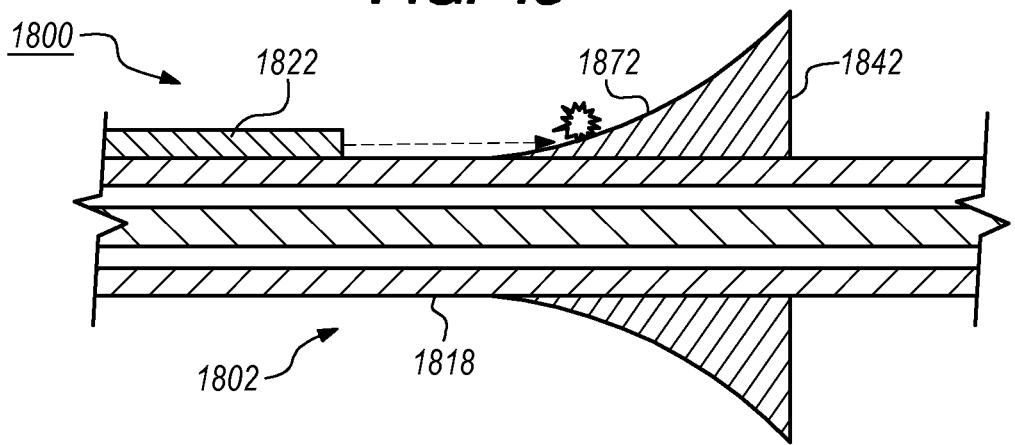
FIG. 18 is a cross-sectional view of a portion of the catheter system including one embodiment of a portion of the catheter.

FIG. 18 is a cross-sectional view of a portion of the catheter system 1800 including one embodiment of a portion of the catheter 1802. In this embodiment, the catheter 1802 can include a guidewire lumen 1818, one or more light guides 1822 and an embodiment of a portion of a plasma target 1842. The plasma target 1842 is spaced apart from the light guide 1822, and includes a target face 1872. The target face 1872 can have any suitable geometry, shape or configuration. In this embodiment, the light guide 1822 and the plasma target 1842 operate substantially similar to those previously shown and/or described. However, in this embodiment, the plasma target 1842 can be annular and can encircle the circumference of the guidewire lumen 1818. Further, the target face 1872 of the plasma target 1842 can have a somewhat concave, conical configuration. In alternative, non-exclusive embodiments, the plasma target 1842 can have a beveled, toroidal or frustoconical configuration, or any other suitable configuration. In an alternative embodiment, the plasma target 1842 only partially encircles the guidewire lumen 1818. Still alternatively, the plasma target 1842 can encircle or partially encircle another structure of the catheter 1802.

Figure 19:
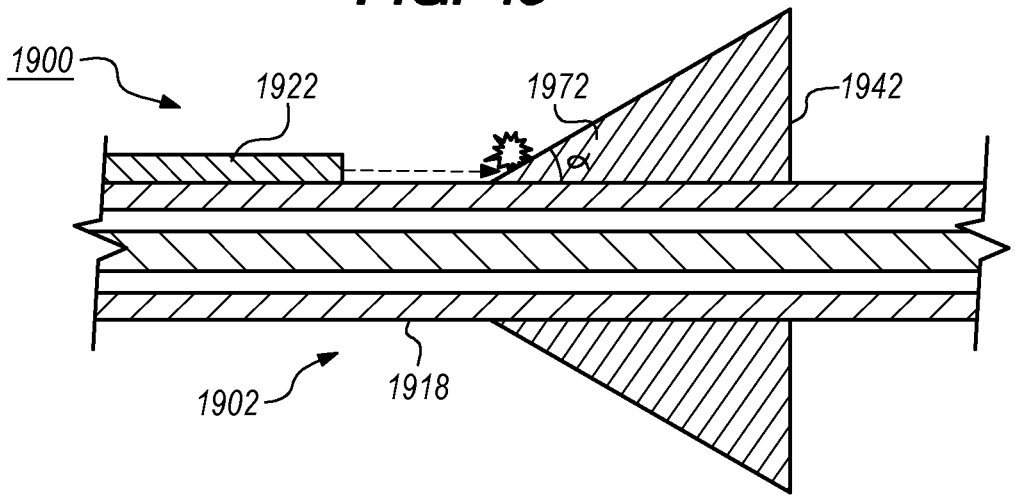
FIG. 19 is a cross-sectional view of a portion of the catheter system including another embodiment of a portion of the catheter.

FIG. 19 is a cross-sectional view of a portion of the catheter system 1900 including one embodiment of a portion of the catheter 1902. In this embodiment, the catheter 1902 can include a guidewire lumen 1918, one or more light guides 1922 and an embodiment of a portion of a plasma target 1942. The plasma target 1942 is spaced apart from the light guide 1922, and includes a target face 1972. The target face 1972 can have any suitable geometry, shape or configuration. In this embodiment, the light guide 1922 and the plasma target 1942 operate substantially similar to those previously shown and/or described. However, in this embodiment, the plasma target 1942 can be annular and can encircle the circumference of the guidewire lumen 1918. Further, the target face 1972 of the plasma target 1942 can have a somewhat conical or pyramidal configuration. In an alternative embodiment, the plasma target 1942 only partially encircles the guidewire lumen 1918. Still alternatively, the plasma target 1942 can encircle or partially encircle another structure of the catheter 1902.

Figure 20:
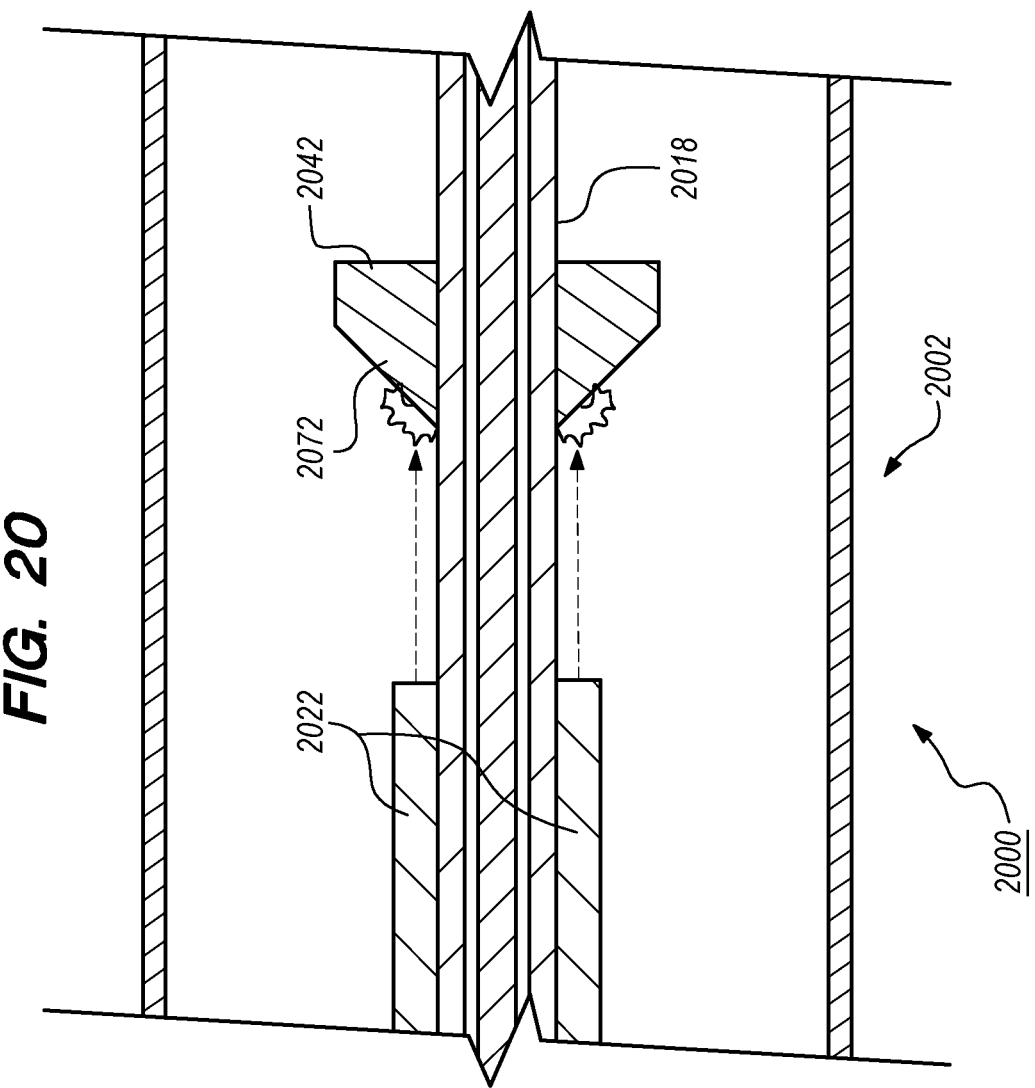
FIG. 20 is a cross-sectional view of a portion of the catheter system including another embodiment of a portion of the catheter.

FIG. 20 is a cross-sectional view of a portion of the catheter system 2000 including one embodiment of a portion of the catheter 2002. In this embodiment, the catheter 2002 can include a guidewire lumen 2018, two or more light guides 2022 (only two light guides 2022 are illustrated in FIG. 20) and an embodiment of a portion of a plasma target 2042. The plasma target 2042 is spaced apart from the light guides 2022, and includes a target face 2072. The target face 2072 can have any suitable geometry, shape or configuration. In this embodiment, the light guides 2022 and the plasma target 2042 operate substantially similar to those previously shown and/or described. In an alternative embodiment, two or more plasma targets 2042 can be secured to the guidewire lumen 2018, wherein each only partially encircles the guidewire lumen 2018. Still alternatively, the plasma target 2042 can encircle or partially encircle another structure of the catheter 2002. It is appreciated that greater than two light guides 2022 can be used with the catheter system 2000 herein. For example, three light guides 2022 can be evenly spaced apart by 120 degrees from one another; four light guides 2022 can be evenly spaced apart by 90 degrees from one another, etc. Still alternatively, any number of light guides 2022 may be positioned so they are not evenly spaced circumferentially around the guidewire lumen 2018.

Figure 21:
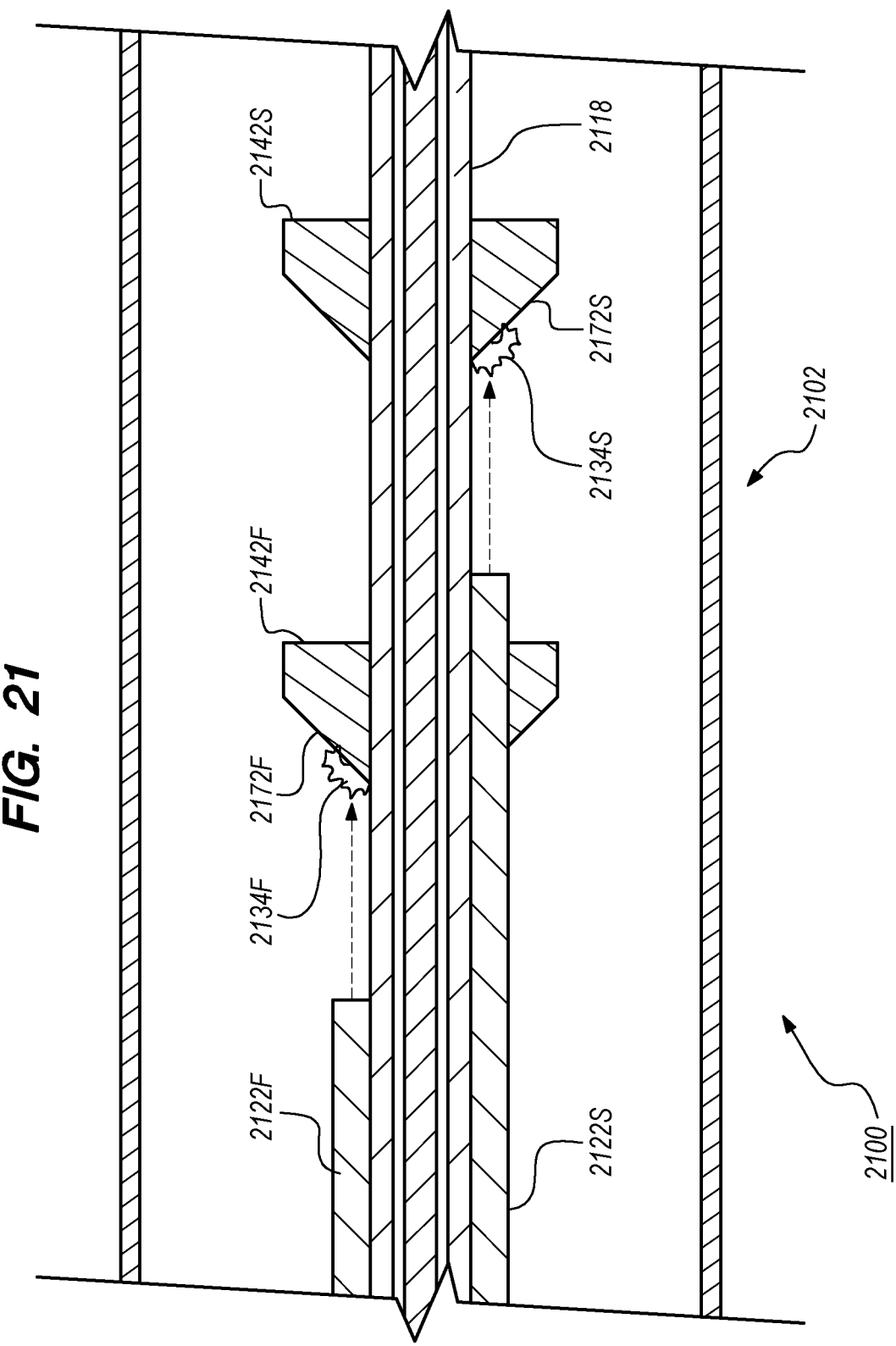
FIG. 21 is a cross-sectional view of a portion of the catheter system including another embodiment of a portion of the catheter.

FIG. 21 is a cross-sectional view of a portion of the catheter system 2100 including one embodiment of a portion of the catheter 2102. In this embodiment, the catheter 2102 can include a guidewire lumen 2118, two or more light guides including a first light guide 2122F, and a second light guide 2122S (only two light guides are illustrated in FIG. 21) and two or more plasma targets including a first plasma target 2142F having a first target face 2172F, and a second plasma target 2142S (only two plasma targets are illustrated in FIG. 21) having a second target face 2172S. In the embodiment illustrated in FIG. 21, the first light guide 2122F emits light energy to generate a first plasma bubble 2134F at or near the first target face 2172F of the first plasma target 2142F. The second light guide 2122S emits light energy to generate a second plasma bubble 2134S at or near the second target face 2172S of the second plasma target 2142S, which is spaced apart from the first plasma target 2142F. In the embodiment illustrated in FIG. 21, the second light guide 2122S extends through the first plasma target 2142F. Alternatively, the second light guide 2122S can traverse around the first plasma target 2142F. Still alternatively, any or all of the plasma targets 2142F, 2142S can either encircle the guidewire lumen 2118, or partially encircle the guidewire lumen 2118.

Balloons

The balloons suitable for use in the catheter systems illustrated and/or described herein include those that can be passed through the vasculature of a patient when in a collapsed configuration. In some embodiments, the balloons illustrated and/or described herein are made from silicone. In other embodiments, the balloons herein are made from polydimethylsiloxane (PDMS), polyurethane, polymers such as PEBAX™ material available from Arkema, which has a location at King of Prussia, Pa., USA, nylon, and the like. In some embodiments, the balloons can include those having diameters ranging from 1 millimeter (mm) to 25 mm in diameter. In some embodiments, the balloons can include those having diameters ranging from at least 1.5 mm to 12 mm in diameter. In some embodiments, the balloons can include those having diameters ranging from at least 1 mm to 5 mm in diameter. In some embodiments, the diameter can be greater than or equal to 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 10.5 mm, 11.0 mm, 11.5 mm, 12.0 mm, 12.5 mm, 13.0 mm, 13.5 mm, 14.0 mm, 14.5 mm, 15.0 mm, 15.5 mm, 16.0 mm, 16.5 mm, 17.0 mm, 17.5 mm, 18.0 mm, 18.5 mm, 19.0 mm, 19.5 mm, or 20.0 mm, or can be an amount falling within a range between any of the foregoing.

In some embodiments, the balloons illustrated and/or described herein can include those having a length ranging from at least 5 mm to 300 mm in length. In some embodiments, the balloons illustrated and/or described herein can include those having a length ranging from at least 8 mm to 200 mm in length. In some embodiments, the length of the balloon can be greater than or equal to 5 mm, 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, 210 mm, 220 mm, 230 mm, 240 mm, 250 mm, 260 mm, 270 mm, 280 mm, 290 mm, or 300 mm, or can be an amount falling within a range between any of the foregoing.

The balloons illustrated and/or described herein can be inflated to inflation pressures from 1 atmosphere (atm) to 70 atm. In some embodiments, the balloons illustrated and/or described herein can be inflated to inflation pressures of from at least 20 atm to 70 atm. In some embodiments, the balloons illustrated and/or described herein can be inflated to inflation pressures of from at least 6 atm to 20 atm. In some embodiments, the balloons illustrated and/or described herein can be inflated to inflation pressures of from at least 3 atm to 20 atm. In some embodiments, the balloons illustrated and/or described herein can be inflated to inflation pressures of from at least 2 atm to 10 atm. In some embodiments, the balloons illustrated and/or described herein can be inflated to inflation pressures that can be greater than or equal to 1 atm, 2 atm, 3 atm, 4 atm, 5 atm, 6 atm, 7 atm, 8 atm, 9 atm, 10 atm, 15 atm, 20 atm, 25 atm, 30 atm, 35 atm, 40 atm, 45 atm, 50 atm, 55 atm, 60 atm, 65 atm, or 70 atm, or can be an amount falling within a range between any of the foregoing.

The balloons illustrated and/or described herein can include those having various shapes, including, but not to be limited to, a conical shape, a square shape, a rectangular shape, a spherical shape, a conical/square shape, a conical/spherical shape, an extended spherical shape, an oval shape, a tapered, shape, a bone shape, a stepped diameter shape, an offset shape, or a conical offset shape. In some embodiments, the balloons illustrated and/or described herein can include a drug eluting coating or a drug eluting stent structure. The drug elution coating or drug eluting stent can include one or more therapeutic agents including anti-inflammatory agents, anti-neoplastic agents, anti-angiogenic agents, and the like.

Balloon Fluids

Exemplary balloon fluids suitable for use herein can include, but are not to be limited to one or more of water, saline, contrast medium, fluorocarbons, perfluorocarbons, gases, such as carbon dioxide, and the like. In some embodiments, the balloon fluids illustrated and/or described herein can be used as base inflation fluids, discussed elsewhere herein. In some embodiments, the balloon inflation fluids include a mixture of saline to contrast medium in a volume ratio of 50:50. In some embodiments, the balloon fluids include a mixture of saline to contrast medium in a volume ratio of 25:75. In some embodiments, the balloon fluids include a mixture of saline to contrast medium in a volume ratio of 75:25. The balloon fluids suitable for use herein can be tailored on the basis of composition, viscosity, and the like in order to manipulate the rate of travel of the pressure waves therein. The balloon fluids suitable for use herein are biocompatible. A volume of balloon fluid can be tailored by the chosen power source and the type of balloon fluid used.

In some embodiments, the contrast agents used in the contrast media herein can include, but are not be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

The balloon fluids illustrated and/or described herein can include those that include absorptive agents that can selectively absorb light in the ultraviolet (e.g., at least 10 nanometers (nm) to 400 nm), visible region (e.g., at least 400 nm to 780 nm), and near-infrared region of the electromagnetic spectrum (e.g., at least 780 nm to 2.5 µm), or in the far-infrared region of the electromagnetic spectrum of at least 10 nm to 2.5 micrometers (µm). Suitable absorptive agents can include those with absorption maxima along the spectrum from at least 10 nm to 2.5 µm. In various embodiments, the absorptive agent can be those that have an absorption maximum matched with the emission maximum of the laser used in the catheter system. By way of non-limiting examples, various lasers described herein can include neodymium:yttrium-aluminum-garnet (Nd:YAG–emission maximum=1064 nm) lasers. holmium:YAG (Ho:YAG–emission maximum=2.1 µm) lasers, or erbium:YAG (Er:YAG–emission maximum=2.94 µm). In some embodiments, the absorptive agents used herein can be water soluble. In other embodiments, the absorptive agents used herein are not water soluble. In some embodiments, the absorptive agents used in the balloon fluids herein can be tailored to match the peak emission of the power source. Various power sources having emission wavelengths of at least 10 nanometers to 1 millimeter are discussed elsewhere herein.

In some embodiments, introduction of the balloon fluid causes the expansion of the balloon from a collapsed configuration to a first expanded configuration and from a first expanded configuration to a second further expanded configuration. In addition, or alternatively, the expansion of the balloon can be accomplished using a shape-memory material or other means.

Light Guides

The light guides illustrated and/or described herein can include an optical fiber or flexible light pipe. The light guides illustrated and/or described herein can be thin and flexible and can allow light signals to be sent with very little loss of strength. The light guides illustrated and/or described herein can include a core surrounded by a cladding about its circumference. In some embodiments, the core can be a cylindrical core or a partially cylindrical core. The core and cladding of the light guides can be formed from one or more materials, including but not limited to one or more types of glass, silica, or one or more polymers. The light guides may also include a protective coating, such as a polymer. It is appreciated that the index of refraction of the core will be greater than the index of refraction of the cladding.

Each light guide can guide light along its length to a distal portion having at least one optical window. The light guides can create a light path as portion of an optical network including a power source. The light path within the optical network allows light to travel from one part of the network to another. Both the optical fiber or the flexible light pipe can provide a light path within the optical networks herein.

The light guides illustrated and/or described herein can assume many configurations about the catheter shaft of the catheters illustrated and/or described herein. In some embodiments, the light guides can run parallel to the longitudinal axis of the catheter shaft of the catheter. In some embodiments, the light guides can be disposed spirally or helically about the longitudinal axis of the catheter shaft of the catheter. In some embodiments, the light guides can be physically coupled to the catheter shaft. In other embodiments, the light guides can be disposed along the length of the outer diameter of the catheter shaft. In yet other embodiments the light guides herein can be disposed within one or more light guide lumens within the catheter shaft. Various configurations for the catheter shafts and light guide lumens will be discussed below.

Diverting Features and Focusing Features

The diverting features suitable for use herein include a reflecting element, a refracting element, and a fiber diffuser. In some embodiments, the diverting feature can be a reflecting element. In some embodiments, the diverting feature can be a refracting element. In some embodiments, the diverting feature can be a fiber diffuser.

A fiber diffuser can direct light from within a light guide to exit at a side surface of the light guide. The fiber diffusers described herein can be created several ways. In some embodiments, the fiber diffusers can be created by micromachining the surface of the distal portion of a light guide with a $CO_2$ laser. In some embodiments, a fused silica coating can be applied to the distal portion of the light guide. In other embodiments, the fiber diffuser can be formed from a glass, a polymer, or a metal coating on the distal portion of the light guide. In other embodiments, the fiber diffuser can be formed by a fiber Bragg grating on the distal portion of the light guide. In some embodiments, the fiber diffuser can include a machined portion of the light guide, a laser-machined portion of the light guide, fiber Bragg gratings, a fused splicing, a fused splicing forming at least one internal mirror, and a splicing of two or more diffuse regions.

Suitable materials for a fiber diffuser can include, but are not be limited to, the materials of the light guide core or light guide cladding, ground glass, silver coated glass, gold coated glass, TiO2, and other materials that will scatter and not significantly absorbed the light wavelength of interest. One method that can be used to create a uniform diffuser in a light guide, optical component, or materials is to utilize scattering centers on the order of at least 50 nanometers to 5 micrometers in size. The scattering centers can have a distribution about 200 nanometers in size.

The diverting features and focusing features suitable for focusing light away from the tip of the light guides herein can include, but are not to be limited to, those having a convex surface, a gradient-index (GRIN) lens, and a mirror focus lens.

Power Sources

The power sources suitable for use herein can include various types of power sources including lasers and lamps. Suitable lasers can include short pulse lasers on the sub-millisecond timescale. In some embodiments, the power source can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid of the catheters illustrated and/or described herein. In various embodiments, the pulse widths can include those falling within a range including from at least 10 ns to 200 ns. In some embodiments, the pulse widths can include those falling within a range including from at least 20 ns to 100 ns. In other embodiments, the pulse widths can include those falling within a range including from at least 1 ns to 5000 ns.

Exemplary nanosecond lasers can include those within the UV to IR spectrum, spanning wavelengths of about 10 nanometers to 1 millimeter. In some embodiments, the power sources suitable for use in the catheter systems herein can include those capable of producing light at wavelengths of from at least 750 nm to 2000 nm. In some embodiments, the power sources can include those capable of producing light at wavelengths of from at least 700 nm to 3000 nm. In some embodiments, the power sources can include those capable of producing light at wavelengths of from at least 100 nm to 10 micrometers (μm). Nanosecond lasers can include those having repetition rates of up to 200 kHz. In some embodiments, the laser can include a Q-switched thulium:yttrium-aluminum-garnet (Tm:YAG) laser. In some embodiments, the laser can include a neodymium:yttrium-aluminum-garnet (Nd:YAG), holmium:yttrium-aluminum-garnet (Ho:YAG), erbium:yttrium-aluminum-garnet (Er:YAG), excimer laser, helium-neon laser, carbon dioxide laser, as well as doped, pulsed, fiber lasers.

Pressure Waves

The catheters illustrated and/or described herein can generate pressure waves having maximum pressures in the range of at least 1 megapascal (MPa) to 100 MPa. The maximum pressure generated by a particular catheter will depend on the power source, the absorbing material, the bubble expansion, the propagation medium, the balloon material, distance of measurement from plasma epicenter, and other factors. In some embodiments, the catheters illustrated and/or described herein can generate pressure waves having maximum pressures in the range of at least 2 MPa to 50 MPa. In other embodiments, the catheters illustrated and/or described herein can generate pressure waves having maximum pressures in the range of at least 2 MPa to 30 MPa. In yet other embodiments, the catheters illustrated and/or described herein can generate pressure waves having maximum pressures in the range of at least 15 MPa to 25 MPa. In some embodiments, the catheters illustrated and/or described herein can generate pressure waves having peak pressures of greater than or equal to 1 MPa, 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 21 MPa, 22 MPa, 23 MPa, 24 MPa, or 25 MPa, 26 MPa, 27 MPa, 28 MPa, 29 MPa, 30 MPa, 31 MPa, 32 MPa, 33 MPa, 34 MPa, 35 MPa, 36 MPa, 37 MPa, 38 MPa, 39 MPa, 40 MPa, 41 MPa, 42 MPa, 43 MPa, 44 MPa, 45 MPa, 46 MPa, 47 MPa, 48 MPa, 49 MPa, or 50 MPa. It is appreciated that the catheters illustrated and/or described herein can generate pressure waves having operating pressures or maximum pressures that can fall within a range, wherein any of the forgoing numbers can serve as the lower or upper bound of the range, provided that the lower bound of the range is a value less than the upper bound of the range.

Therapeutic treatment can act via a fatigue mechanism or a brute force mechanism. For a fatigue mechanism, operating pressures would be about at least 0.5 MPa to 2 MPa, or about 1 MPa. For a brute force mechanism, operating pressures would be about at least 20 MPa to 30 MPa, or about 25 MPa. Pressures between the extreme ends of these two ranges may act upon a treatment site using a combination of a fatigue mechanism and a brute force mechanism.

The pressure waves described herein can be imparted upon the treatment site from a distance within a range from at least 0.1 millimeters (mm) to 25 mm extending radially from a longitudinal axis of a catheter placed at a treatment site. In some embodiments, the pressure waves can be imparted upon the treatment site from a distance within a range from at least 10 mm to 20 mm extending radially from a longitudinal axis of a catheter placed at a treatment site. In other embodiments, the pressure waves can be imparted upon the treatment site from a distance within a range from at least 1 mm to 10 mm extending radially from a longitudinal axis of a catheter placed at a treatment site. In yet other embodiments, the pressure waves can be imparted upon the treatment site from a distance within a range from at least 1.5 mm to 4 mm extending radially from a longitudinal axis of a catheter placed at a treatment site. In some embodiments, the pressure waves can be imparted upon the treatment site from a range of at least 2 MPa to 30 MPa at a distance from 0.1 mm to 10 mm. In some embodiments, the pressure waves can be imparted upon the treatment site from a range of at least 2 MPa to 25 MPa at a distance from 0.1 mm to 10 mm. In some embodiments, the pressure waves can be imparted upon the treatment site from a distance that can be greater than or equal to 0.1 mm, 0.2 mm, 0.3 mm, 0.4 mm, 0.5 mm, 0.6 mm, 0.7 mm, 0.8 mm, or 0.9 mm, 1 mm, 2 mm, 3 mm, 4 mm, 5 mm, 6 mm, 7 mm, 8 mm, 9 mm, or 10 mm, or can be an amount falling within a range between any of the foregoing.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

As used herein, the recitation of numerical ranges by endpoints shall include all numbers subsumed within that range, inclusive (e.g., 2 to 8 includes 2, 2.1, 2.8, 5.3, 7, 8, etc.).

It is recognized that the figures shown and described are not necessarily drawn to scale, and that they are provided for ease of reference and understanding, and for relative positioning of the structures.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a blood vessel, the catheter system comprising:
a power source;
a light guide that receives power from the power source, the light guide having a distal tip, the light guide emitting light energy in a direction away from the distal tip; and
a plasma target that is spaced apart from the distal tip of the light guide by a target gap distance, the plasma target being configured to receive light energy from the light guide so that a plasma is generated at the plasma target upon receiving the light energy from the light guide, the plasma target being at least partially formed from one of tungsten, tantalum, platinum, molybdenum, niobium, and iridium.

2. The catheter system of claim 1 wherein the power source is a laser and the light guide is an optical fiber.

3. The catheter system of claim 1 further comprising an inflatable balloon that encircles the distal tip of the light guide, the plasma target being positioned within the inflatable balloon.

4. The catheter system of claim 1 wherein the target gap distance is greater than 1 μm.

5. The catheter system of claim 1 wherein the target gap distance is greater than 100 μm.

6. The catheter system of claim 1 wherein the plasma target has one of a substantially circular, square, rectangular, oval, pentagonal, hexagonal, octagonal, polygonal, trapezoidal or diamond-shaped cross-sectional configuration.

7. The catheter system of claim 1 further comprising a guidewire lumen, the light guide being coupled to the guidewire lumen.

8. The catheter system of claim 1 wherein the plasma target has a target face that receives the light energy from the light guide, the target face being angled relative to a direction the light energy is emitted to the plasma target.

9. The catheter system of claim 8 wherein the target face has an angle that is greater than zero degrees and less than 180 degrees relative to a direction the light energy is emitted to the plasma target.

10. The catheter system of claim 8 wherein the plasma target has a target face that receives the light energy from the light guide, the target face having an angle that is greater than approximately 45 degrees and less than approximately 135 degrees relative to a direction the light energy is emitted to the plasma target.

11. The catheter system of claim 1 wherein the light guide includes a distal region having a longitudinal axis, and wherein the direction the light energy is emitted is substantially along the longitudinal axis of the distal region.

12. The catheter system of claim 1 wherein the light guide includes a distal region having a longitudinal axis, and wherein the direction the light energy is emitted is angled relative to the longitudinal axis of the distal region.

13. The catheter system of claim 1 further comprising a plurality of plasma targets that are spaced apart from the distal tip of the light guide, at least one of the plurality of plasma targets being configured to receive light energy from the light guide.

14. The catheter system of claim 1 wherein the plasma target is further partially formed from one of magnesium oxide, beryllium oxide, tungsten carbide, titanium nitride, titanium carbonitride and titanium carbide.

15. The catheter system of claim 1 wherein the plasma target is further partially formed from a ceramic material.

16. The catheter system of claim 1 wherein the plasma target is mechanically coupled to the light guide.

17. The catheter system of claim 1 wherein the plasma target is mechanically uncoupled from the light guide.

18. The catheter system of claim 1 further comprising a guidewire lumen, wherein the plasma target at least partially encircles the guidewire lumen.

19. The catheter system of claim 1 wherein the plasma target has a target face that receives light energy from the light guide, the target face including one or more surface features.

20. The catheter system of claim 19 wherein the one or more surface features includes at least one of an indentation and a projection.

21. The catheter system of claim 19 wherein the target face includes one of a beveled edge, a conical configuration, a pyramidal configuration, a dome-shaped configuration, a concave configuration, a convex configuration, a multi-faceted configuration, a coiled configuration, a spring-like configuration, and a somewhat spiral configuration.

22. The catheter system of claim 1 wherein the plasma target is movable relative to the light guide.

23. The catheter system of claim 1 wherein the plasma target is spring-loaded.

24. The catheter system of claim 1 further comprising a guidewire lumen, wherein the plasma target is coupled to the guidewire lumen.

25. The catheter system of claim 1 further comprising a second light guide that receives power from the power source, the second light guide having a second distal tip, the second light guide emitting light energy in a direction away from the second distal tip toward the plasma target, the plasma target being spaced apart from the second distal tip of the second light guide, the plasma target being configured to receive light energy from the second light guide so that a second plasma is generated at the plasma target upon receiving the light energy from the second light guide.

26. The catheter system of claim 1 further comprising a second light guide and a second plasma target, the second light guide receiving power from the power source, the second light guide having a second distal tip, the second light guide emitting light energy in a direction away from the second distal tip toward the second plasma target, the second plasma target being spaced apart from the plasma target and the second distal tip of the second light guide, the second plasma target being configured to receive light energy from the second light guide so that a second plasma is generated at the second plasma target upon receiving the light energy from the second light guide.

27. A catheter system for treating a treatment site within or adjacent to a blood vessel, the catheter system comprising:
　a power source;
　a light guide that receives power from the power source, the light guide having a distal tip, the light guide emitting light energy in a direction away from the distal tip; and
　a plasma target that is secured to the light guide, the plasma target being at least partially formed from one of tungsten, tantalum, platinum, molybdenum, niobium, and iridium, the plasma target including a target face that is spaced apart from the distal tip of the light guide by a target gap distance, the target face being configured to receive light energy from the light guide so that a plasma is generated at the target face upon receiving the light energy from the light guide, the target face being angled relative to a direction the light energy is emitted to the plasma target.

28. The catheter system of claim 3 wherein the balloon includes a drug-eluting coating.

29. A catheter system for treating a treatment site within or adjacent to a blood vessel, the catheter system comprising:
　a power source;
　a light guide that receives power from the power source, the light guide having a distal tip, the light guide emitting light energy in a direction away from the distal tip; and
　a plasma target that is spaced apart from the distal tip of the light guide by a target gap distance, the plasma target being configured to receive light energy from the light guide so that a plasma is generated at the plasma target upon receiving the light energy from the light guide, the plasma target having a substantially circular cross-sectional shape.

30. The catheter system of claim 29 wherein the plasma target is at least partially formed from one of tungsten, tantalum, platinum, molybdenum, niobium, and iridium.

* * * * *